(12) United States Patent
Crawford et al.

(10) Patent No.: US 9,499,836 B2
(45) Date of Patent: Nov. 22, 2016

(54) FERTILIZATION AND FRUIT SIZE

(75) Inventors: Brian C. W. Crawford, San Diego, CA (US); Martin F. Yanofsky, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 261 days.

(21) Appl. No.: 14/119,426

(22) PCT Filed: May 31, 2012

(86) PCT No.: PCT/US2012/040294
§ 371 (c)(1),
(2), (4) Date: Feb. 12, 2014

(87) PCT Pub. No.: WO2012/166978
PCT Pub. Date: Dec. 6, 2012

(65) Prior Publication Data
US 2014/0245490 A1    Aug. 28, 2014

Related U.S. Application Data

(60) Provisional application No. 61/491,574, filed on May 31, 2011.

(51) Int. Cl.
*C12N 15/87* (2006.01)
*C12N 15/82* (2006.01)
*C07K 14/415* (2006.01)

(52) U.S. Cl.
CPC ......... *C12N 15/8287* (2013.01); *C07K 14/415* (2013.01); *C12N 15/829* (2013.01); *C12N 15/8249* (2013.01); *C12N 15/8261* (2013.01)

(58) Field of Classification Search
None
See application file for complete search history.

(56) References Cited

U.S. PATENT DOCUMENTS

2009/0094717 A1* 4/2009 Troukhan ............. C07K 14/415
800/290

FOREIGN PATENT DOCUMENTS

GB   WO 2007063289 A2 *  6/2007   ........... C07K 14/415
WO   WO 2007/063289 A2 *  6/2007

OTHER PUBLICATIONS

Skinner et al, Differentiation (2010) 80: 1-8.*
Yokota, Trends in Plant Science (1997) 2: 137-143.*
Alvarez, J., et al., *Crabs claw and Spatula genes regulate growth and pattern formation during gynoecium development in Arabidopsis thaliana*, (2002) Int. J. Plant Sci. 63(1):17-41.

Carbonell-Bejerano, P. et al., *A Fertilization-Independent Developmental Program Triggers Partial Fruit Development and Senescence Processes in Pistils of Arabidopsis*, (2010) Plant Physiol. 154:163-72.
Crawford, B. C. et al., *The Formation and Function of the Female Reproductive Tract in Flowering Plants*, (2008) Current Biology 18:R972-8.
Crawford, B. C. et al., *The NTT Gene Is Required for Transmitting-Tract Development in Carpels of Arabidopsis thaliana*, (2007) Curr. Biol. 17:1101-8.
Friedrichsen, D. M., et al., *Three redundant brassinosteroid early response genes encode putative bHLH transcription factors required for normal growth*, (2002) Genetics 162:1445-56.
Goetz, M. et al., *Auxin Response Factor8 Is a Negative Regulator of Fruit Initiation in Arabidopsis*, (2006) Plant Cell 18:1873-86.
Goetz, M. et al., *Expression of Aberrant Forms of Auxin Response Factor8 Stimulates Parthenocarpy in Arabidopsis and Tomato*, (2007) Plant Physiol. 145:351-66.
Gremski, K. et al., *The HECATE genes regulate female reproductive tract development in Arabidopsis thaliana*, (2007) Development 134:3593-3601.
Heisler, M. G. et al., *SPATULA, a gene that controls development of carpel margin tissues in Arabidopsis, encodes a bHLH protein*, (2001) Development 128:1089-98.
Ichihashi Y., et al., *The bHLH Transcription Factor SPATULA Controls Final Leaf Size in Arabidopsis thaliana*, (2010) Plant and Cell Physiology 51:252-261.
Liljegren, S.J. et al., *Control of fruit patterning in Arabidopsis by Indehiscent*, (2004) Cell 116: 843-53.
Nagpal, P. et al., *Auxin response factors ARF6 and ARF8 promote jasmonic acid production and flower maturation*, (2005) Development 132:4107-18.
Palanivelu, R. et al., *Distinct short-range ovule signals attract or repel Arabidopsis thaliana pollen tubes in vitro*, (2006) BMC Plant Biol. 6:7.
Poppenberger B. et al., *CESTA, a positive regulator of brassinosteroid Biosynthesis*, (2011) The EMBO Journal 30:1149-61.
Qin Y. et al., *Penetration of the Stigma and Style Elicits a Novel Transcriptome in Pollen Tubes*, (2009) PLoS Genetics 5, Article No. e1000621.
Savaldi-Goldstein S. et al., *The epidermis both drives and restricts plant shoot growth.*, (2007) Nature (London) 446:199-202.
Sessions, A. et al., *Cell-cell signaling and movement by the floral transcription factors LEAFY and APETALA1*, (2000) Science's STKE 289:779-781.
Sessions, A. et al., *The Arabidopsis thaliana Meristem Layer 1 promoterspecies epidermal expression in meristems and young primordia*, (1999) The Plant Journal 20:259-263.
Sorefan, K. et al., *A regulated auxin minimum is required for seed dispersal in Arabidopsis*, (2009) Nature (London) 459:583.
Sundberg, E. et al., *Distinct and Dynamic Auxin Activities During Reproductive Development*, (2009) Cold Spring Harb. Perspect Biol. 1: a001628.
Vivian-Smith, A. et al., *Fruit development is actively restricted in the absence of fertilization in Arabidopsis*, (2001) Development 128: 2321-31.

(Continued)

*Primary Examiner* — Stuart F Baum
(74) *Attorney, Agent, or Firm* — Kilpatrick Townsend & Stockton LLP

(57) ABSTRACT

Plants having modulated expression of a HAF or BEE polypeptide and which modulate aspects of plant fertility, such as parthenocarpy, fertilization efficiency, and/or fruit size, are described. Methods of modulating fertility characteristics in a plant by modulating the expression of a HAF or BEE polypeptide in the plant are also described.

14 Claims, 15 Drawing Sheets

(56) References Cited

OTHER PUBLICATIONS

Wang, H. et al., *Regulation of Arabidopsis Brassinosteroid Signaling by Atypical Basic Helix-Loop-Helix Proteins,* (2009) Plant Cell 21:3781-3791.

Williams, J. H., *Amborella Trichopoda (Amborellaceae) and the Evolutionary Developmental Origins of the Angiosperm Progamic Phase,* (2009) American Journal of Botany 96:144-165.

Williams, J. H., *Novelties of the flowering plant pollen tube underlie diversification of a key life history stage,* (2008) Proc. Natl. Acad. Sci. USA 105:11259-63.

Wu, M. F. et al., *Arabidopsis micro RNA167 controls patterns of ARF6 and ARF8 expression and regulates both female and male reproduction,* (2006) Development 133:4211-8.

Declaration of Non-Establishment of International Search Report, PCT/US2012/040294, mailed Mar. 28, 2013, 5 pages.

\* cited by examiner

FERTILIZATION AND FRUIT SIZE

CROSS-REFERENCE TO RELATED APPLICATIONS

This application is a U.S. national stage application under 35 U.S.C. §371 of International Application No. PCT/US2012/040294, filed May 31, 2012, which claims priority to U.S. Provisional Application No. 61/491,574, filed May 31, 2011, the entire content of each of which is incorporated by reference herein for all purposes.

STATEMENT AS TO RIGHTS TO INVENTIONS MADE UNDER FEDERALLY SPONSORED RESEARCH OR DEVELOPMENT

This invention was made with Government support under the National Science Foundation (NSF IOS0817544). The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-54-1.TXT, created on Apr. 29, 2014, 24,576 bytes, machine format IBM-PC, MS-Windows operating system, is hereby incorporated by reference in its entirety for all purposes.

BACKGROUND OF THE INVENTION

Throughout plant evolution the egg cell has become progressively less exposed to fertilization by the male gametophyte. Indeed, the defining feature of angiosperms is the enclosure of the ovule within a carpel. This presents a problem of accessibility for pollen tubes (Crawford, B. C. and Yanofsky, M. F., *Curr Biol* 18:R972-8 (2008); Williams, J. H., *American Journal of Botany* 96:144 (2009)). Not only are ovules distant from the point of pollen germination, in some angiosperms, such as *Arabidopsis*, the ovule is buried within the layers of tissue of the carpel. Additionally, the pollination and fertilization process occurs more rapidly in angiosperms compared with gymnosperms (Williams, J. H., *Proc Natl Acad Sci USA* 105:11259-63 (2008); Williams, J. H., *American Journal of Botany* 96:144 (2009)). To overcome these difficulties, angiosperms have developed a unique set of tissues to assist pollen tubes in reaching the ovules. These tissues are collectively known as the reproductive tract and consist of the stigma, style, transmitting tract and funiculus (FIG. 1A,B).

Pollen grains initially contact and germinate on elongated papillary cells of the stigma. Once germinated, they develop into pollen tubes that grow into the style, the connecting tissue between the stigma and ovary chamber (FIG. 1A,B). In *Arabidopsis thaliana*, pollen tubes must grow through the short, enclosed style to reach the ovary (Lennon, K. et al., *Sexual Plant Reproduction* 11:49-59 (1998)). In other angiosperms, however, such as lily, pollen tubes can grow on the surface of an open style to reach the ovary (Kim, S. et al., *Proc Natl Acad Sci USA* 100:16125-30 (2003)). The closed style of *Arabidopsis* contains the start of the transmitting tract, a pathway for pollen tube growth that undergoes programmed cell death (Crawford, B. C. et al., *Curr Biol* 17:1101-8 (2007)). Transmitting tract tissue develops in the center of the septum between the two fused carpels (FIG. 1A) and connects the style to bottom of the ovary chamber (FIG. 1B). Pollen tubes grow basally through the transmitting tract and exit laterally onto the septum epidermis, whereupon they grow towards and upon funiculi to reach ovules. The funiculus develops at the boundary of the septum and carpel walls and connects the ovules to the carpel (FIG. 1A). At the end of the funiculus, pollen tubes enter the micropyle to fertilize the egg cell.

The reproductive tract is essential for successful fertilization of ovules by pollen, and seed set is reduced in mutants that interfere with reproductive tract development (Alvarez, J. and Smyth, D. R., *Int. J. Plant Sci.* 163:17-41 (2002); Gremski, K. et al., *Development* 134:3593-601 (2007); Heisler, M. G. et al., *Development* 128:1089-98 (2001)). Pollen tubes also target ovules more efficiently in vitro if they have first grown through stigma and style (Palanivelu, R. and Preuss, D. *BMC Plant Biol* 6:7 (2006)).

The HECATE (HEC1, HEC2, HEC3) and SPATULA (SPT) genes encode putative bHLH transcription factors that play key roles in reproductive tract development since they control overall growth of the stigma, style and transmitting tract. Mutations in these genes lead to varying degrees of reduced fertility, and while HEC2-RNAi hec1 hec3 mutants are completely infertile, spt mutants show moderate infertility (Alvarez, J. and Smyth, D. R., *Int. J. Plant Sci.* 163:17-41 (2002); Gremski, K. et al., *Development* 134:3593-601 (2007); Heisler, M. G. et al., *Development* 128:1089-98 (2001)). HEC and SPT proteins have been shown to interact, suggesting that they act together to control development. Although the entire reproductive tract is affected in these mutants, mutations in other genes show more specific defects in reproductive tract differentiation. The NO TRANSMITTING TRACT (NTT) gene, for example, is required for normal differentiation of the ovary transmitting tract. Transmitting tract cells normally produce an extracellular matrix (ECM) containing a mixture of glycoproteins, glycolipids and polysaccharides Lennon, K. et al., *Sexual Plant Reproduction* 11:49-59 (1998)). The specific contribution of ECM to pollen tube growth is unknown, but growth studies have demonstrated that pollen tubes grow faster in vivo than in vitro, and this has been speculated to be due to interactions with ECM (Palanivelu, R. and Preuss, D. *BMC Plant Biol* 6:7 (2006)). Transmitting tract cells also undergo a process of programmed cell death essential for efficient pollen tube growth. In the ntt mutant, both ECM production and cell death are absent from the ovary transmitting tract. As a result, pollen tubes progress normally through the style but have great difficulty entering the ovary and the basal ovules remain unfertilized (Crawford, B. C. et al., *Curr Biol* 17:1101-8 (2007)).

SUMMARY OF THE INVENTION

In one aspect, the present invention provides plants (or plant cells, seeds, flowers, leaves, or fruit from said plants) exhibiting one or more modulated fertility characteristics. In some embodiments, the plant has modulated expression of a polypeptide substantially (e.g., at least 60%, 70%, 80%, 90%, 91%, 92%, 93%, 94%, 95%, 96%, 97%, 98%, or 99%) identical to SEQ ID NO:2, 4, 6, 8, or 10. In some embodiments, the plant comprises a heterologous expression cassette comprising a promoter operably linked to a polynucleotide, which polynucleotide when expressed in the plant modulates expression of a polypeptide substantially identical to SEQ ID NO:2, 4, 6, 8, or 10, wherein the plant exhibits one or more modulated fertility characteristics as compared to a non-transgenic control plant.

In some embodiments, expression of the polypeptide in the plant is increased compared to expression of the polypeptide in a non-transgenic control plant, wherein the plant is characterized by having increased fertilization efficiency, increased fruit size, and/or parthenocarpy. In some embodiments, wherein expression of the polypeptide in the plant is increased compared to expression of the polypeptide in a non-transgenic control plant, the transgenic plant comprises an expression cassette comprising a promoter operably linked to a polynucleotide encoding a polypeptide that is identical to or substantially identical to SEQ ID NO:2, 4, 6, 8, or 10. In some embodiments, the polynucleotide encodes a polypeptide is substantially identical to SEQ ID NO:2. In some embodiments, the polynucleotide encodes the polypeptide of SEQ ID NO:2. In some embodiments, the expression cassette is a heterologous expression cassette.

In some embodiments, expression of the polypeptide in the plant is decreased compared to expression of the polypeptide in a non-transgenic control plant, wherein the plant is characterized by reduced fertility. In some embodiments, wherein expression of the polypeptide in the transgenic plant is decreased as compared to a non-transgenic control plant, the polynucleotide inhibits expression of a polypeptide that is identical to or substantially identical to SEQ ID NO:2, 4, 6, 8, or 10. In some embodiments, the polynucleotide inhibits expression of a polypeptide that is substantially identical to SEQ ID NO:2. In some embodiments, wherein the expression of the polypeptide in the plant is decreased compared to expression of the polypeptide in a non-transgenic control plant, the polynucleotide that decreases expression of the polypeptide is in a sense direction compared to the promoter. In some embodiments, the polynucleotide that decreases expression of the polypeptide is in an antisense direction compared to the promoter. In some embodiments, the plant has inhibited expression of two or more polypeptides that are identical to or substantially identical to SEQ ID NO:2, 4, 6, 8, or 10. In some embodiments, the plant comprises a polynucleotide that inhibits expression of a polypeptide that is identical to or substantially identical to SEQ ID NO:2, and the plant further comprises a polynucleotide that inhibits expression of a polypeptide that is identical to or substantially identical to SEQ ID NO:4 and/or SEQ ID NO:6.

In some embodiments, the promoter is a constitutive promoter. In some embodiments, the promoter is not a constitutive promoter. In some embodiments, the promoter is a tissue-specific promoter. In some embodiments, the tissue-specific promoter is a reproductive tissue-specific promoter. In some embodiments, the tissue-specific promoter is a floral part-specific promoter. In some embodiments, the tissue-specific promoter is an epidermal-specific promoter.

In some embodiments, the plant is a fruit-bearing crop plant.

In another aspect, the present invention provides expression cassettes, and expression vectors comprising said expression cassettes, for modulating one or more fertility characteristics in a plant. In some embodiments, the expression cassette comprises a promoter operably linked to a polynucleotide, which polynucleotide when expressed in the plant modulates expression of a polypeptide substantially identical to SEQ ID NO:2, 4, 6, 8, or 10, wherein the plant exhibits one or more modulated fertility characteristics as compared to a non-transgenic control plant.

In some embodiments, the expression cassette comprises a polynucleotide that encodes a polypeptide identical to or substantially identical to SEQ ID NO:2, 4, 6, 8, or 10, wherein introduction of the expression cassette into a plant results in the plant having increased fertilization efficiency, increased fruit size, and/or parthenocarpy as compared to a plant lacking the expression cassette.

In some embodiments, the expression cassette comprises a polynucleotide that decreases expression of a polypeptide identical to or substantially identical to SEQ ID NO:2, 4, 6, 8, or 10, wherein introduction of the expression cassette into a plant results in the plant having decreased fertility as compared to a plant lacking the expression cassette.

In some embodiments, the expression cassette comprises a polynucleotide that modulates expression of a polypeptide that is substantially identical to SEQ ID NO:2. In some embodiments, the expression cassette comprises a polynucleotide that modulates expression of the polypeptide of SEQ ID NO:2.

In another aspect, the present invention provides methods of generating a plant characterized by one or more modulated fertility characteristics. In some embodiments, the one or more modulated fertility characteristics are selected from increased fertilization efficiency, increased fruit size, and/or parthenocarpy. In some embodiments, the method comprises:

introducing an expression cassette in a plurality of plants, the expression cassette comprising a promoter operably linked to a polynucleotide encoding a polypeptide identical to or substantially (e.g., at least 60%, 70%, 80%, 90%, 91%, 92%, 93%, 94%, 95%, 96%, 97%, 98%, or 99%) identical to SEQ ID NO:2, 4, 6, 8, or 10; and selecting a plant characterized by having increased fertilization efficiency, increased fruit size, and/or parthenocarpy as compared to a control plant.

In some embodiments, the polynucleotide encodes a polypeptide substantially identical to SEQ ID NO:2. In some embodiments, the polynucleotide encodes the polypeptide of SEQ ID NO:2.

In some embodiments, the one or more modulated fertility characteristics is decreased fertility. In some embodiments, the method comprises:

introducing an expression cassette in a plurality of plants, the expression cassette comprising a promoter operably linked to a polynucleotide that inhibits expression of a polypeptide identical to or substantially (e.g., at least 60%, 70%, 80%, 90%, 91%, 92%, 93%, 94%, 95%, 96%, 97%, 98%, or 99%) identical to SEQ ID NO:2, 4, 6, 8, or 10; and selecting a plant characterized by having decreased fertility as compared to a control plant.

In some embodiments, the polynucleotide inhibits a polypeptide that is substantially identical to SEQ ID NO:2. In some embodiments, the polynucleotide inhibits the polypeptide of SEQ ID NO:2.

In some embodiments, the polynucleotide comprises at least a portion (e.g., at least 20, 50, 75, 100, 125, 150, 175, 200 contingous nucleotides or more) of any of SEQ ID NOs:1, 3, 5, 7, or 9 or a complement thereof.

DEFINITIONS

Figure 1:
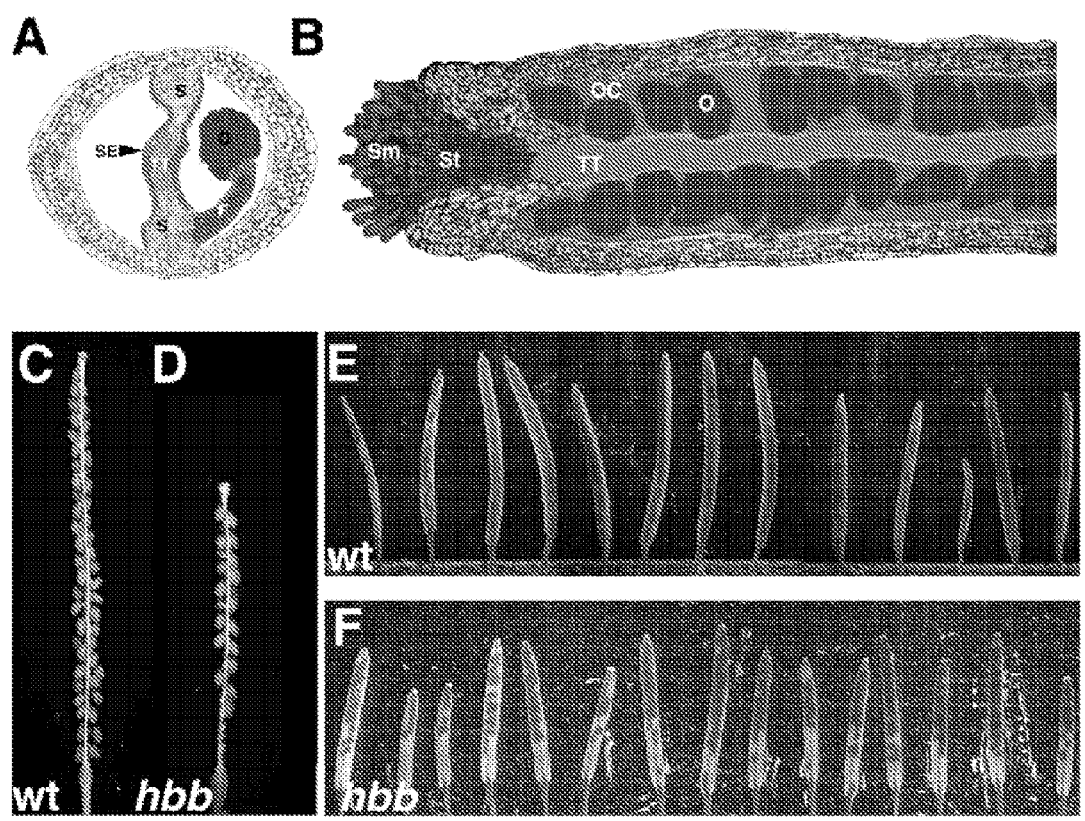
FIG. 1. Reproductive Tract Structure and haf bee1 bee3 (hbb) Mutant Phenotype. (A) Cross section of carpel with structures colored. Transmitting tract (TT) is blue, septum (S) yellow, septum epidermis (SE) orange, funiculus (F) green and ovule (0) maroon. (B) Longitudinal section of carpel with structures colored. In addition to the structures labeled in (A), the ovary chamber (OC) is green, the style (St) dark blue and stigma (Sm) red. (C) Wild-type seed set showing equivalent apical and basal seed distribution (D) haf bee1 bee3 mutant seed set showing a loss of basal seeds. (E) Wild-type siliques showing seeds uniformly distributed throughout fruit. (F) haf bee1 bee3 mutant siliques showing consistent loss of basal seeds.

The term "fertility characteristic" refers to a characteristic of a plant that relates to one or more aspects of ovule fertilization, seed development, and/or fruit production in the plant. A "modulated fertility characteristic" in a transgenic plant of the present invention refers to a fertility characteristic that is increased, enhanced, decreased, or inhibited in a transgenic plant as compared to a non-transgenic control plant. Fertility characteristics that can be modulated according to the compositions and methods of the present invention include, but are not limited to, fertilization efficiency, fruit production in the absence of fertilization (i.e., parthenocarpy), or fruit size. In some embodiments, the fertility characteristic (e.g., fertilization efficiency, parthenocarpy, and/or fruit size) is increased or enhanced in a transgenic plant as compared to a non-transgenic control plant. In some embodiments, the fertility characteristic (e.g., fertilization efficiency, parthenocarpy, and/or fruit size) is decreased or inhibited in a transgenic plant as compared to a non-transgenic control plant.

The term "modulated fertilization efficiency" refers to an alteration (e.g., increase or decrease) in the number of carpels that are fertilized in a plant, i.e., the number of carpels that produce seeds. In some embodiments, modulated fertilization efficiency is measured by determining the number of carpels that are fertilized (e.g., fertilized siliques) under minimal pollination for a transgenic plant as compared to a control non-transgenic plant. As used herein, fertilization efficiency is "increased" in a transgenic plant of the present invention if the number of fertilized siliques per plant is at least about 10%, 15%, 20%, 25%, 30%, 40%, 50%, 60%, 70%, 80%, or 90% more than the number of fertilized siliques per plant produced by a non-transgenic control plant. As used herein, fertilization efficiency is "decreased' in a transgenic plant of the present invention if the number of fertilized siliques per plant produced by the transgenic plant is about 90%, 80%, 70%, 60%, 50%, 40%, 30%, 20%, or 10% less than the number of fertilized siliques per plant produced by a control plant.

The terms "nucleic acid" and "polynucleotide" are used synonymously and refer to a single or double-stranded polymer of deoxyribonucleotide or ribonucleotide bases read from the 5' to the 3' end. Nucleic acids or polynucleotides may also include modified nucleotides that permit correct read through by a polymerase and do not alter expression of a polypeptide encoded by that nucleic acid. "Polynucleotide sequence" or "nucleic acid sequence" may include both the sense and antisense strands of a nucleic acid as either individual single strands or in the duplex.

The phrase "nucleic acid sequence encoding" refers to a nucleic acid that codes for an amino acid sequence of at least 5, 10, 15, 20, 25, 30, 35, 40, 45, 50, or more contiguous amino acids within one reading frame. The amino acid need not necessarily be expressed when introduced into a cell or other expression system, but may merely be determinable based on the genetic code. For example, the sequence ATGATGGAGCATCAT (SEQ ID NO:11) encodes MMEHH (SEQ ID NO:12). Thus, a polynucleotide may encode a polypeptide sequence that comprises a stop codon or contains a changed frame so long as there are at least 5, 10, 15, 20, 25, 30, 35, 40, 45, 50, or more contiguous amino acids within one reading frame. The nucleic acid sequences may include both the DNA strand sequence that is transcribed into RNA and the RNA sequence that is translated into protein. The nucleic acid sequences include both the full length nucleic acid sequences as well as fragments from the full length sequences. It should be further understood that the sequence includes the degenerate codons of the native sequence or sequences which may be introduced to provide codon preference in a specific host cell.

The term "promoter," as used herein, refers to a polynucleotide sequence capable of driving transcription of a coding sequence in a cell. Thus, promoters used in the polynucleotide constructions of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. Such promoters need not be of plant origin, for example, promoters derived from plant viruses, such as the CaMV35S promoter, can be used in the present invention. A "constitutive promoter" is one that is capable of initiating transcription in nearly all tissue types, whereas a "tissue-specific promoter" initiates transcription only in one or a few particular tissue types.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "seed plant" means an angiosperm or gymnosperm. An angiosperm is a seed-bearing plant whose seeds are borne in a mature ovary (fruit). An angiosperm commonly is recognized as a flowering plant. Angiosperms are divided into two broad classes based on the number of cotyledons, which are seed leaves that generally store or absorb food. Thus, a monocotyledonous angiosperm is an angiosperm having a single cotyledon, whereas a dicotyledonous angiosperm is an angiosperm having two cotyledons. A variety of angiosperms are known including, for example, oilseed plants, leguminous plants, fruit-bearing plants, ornamental flowers, cereal plants and hardwood trees, which general classes are not necessarily exclusive. The skilled artisan will recognize that the methods of the invention can be practiced using these or other angiosperms, as desired. A gymnosperm is a seed-bearing plant with seeds not enclosed in an ovary.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

Two nucleic acid sequences or polypeptides are said to be "identical" if the sequence of nucleotides or amino acid residues, respectively, in the two sequences is the same when aligned for maximum correspondence as described below.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity," used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. Accordingly, sequences of the invention include nucleic acid sequences or polypeptides that have substantial identity to SEQ ID NO:1, 2, 3, 4, 5, 6, 7, 8, 9, or 10. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, polypeptides which are "substantially similar" share sequences as noted above except that residue positions which are not identical may differ by conservative amino acid changes. Conservative amino acid substitutions refer to the interchangeability of residues having similar side chains. One of skill will recognize that an individual substitution in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

The term "complementary to" or "complement of" is used herein to mean that a polynucleotide sequence is complementary to all or a portion of (e.g., at least 25, at least 50, at least 75, at least 100, at least 125, at least 150, at least 175, at least 200, or more contiguous nucleotides of) a reference polynucleotide sequence.

DETAILED DESCRIPTION OF THE INVENTION

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y., (1989) and Current Protocols in Molecular Biology, F. M. Ausubel et al., eds., Current Protocols, a joint venture between Greene Publishing Associates, Inc. and John Wiley & Sons, Inc., (supplemented through 2004).

I. Introduction

As described in the Examples section below, the inventors have found that the closely related basic helix-loop-helix (bHLH) transcription factors HALF FILLED (HAF), BRASSINOSTEROID ENHANCED EXPRESSION 1 (BEE1), and BRASSINOSTEROID ENHANCED EXPRESSION 3 (BEE3) are all expressed in overlapping patterns in the reproductive tract. From loss-of-function and ectopic expression assays, the inventors have further found that HAF, BEE1, and BEE3 are involved in the development of the reproductive tract and in fertilization. Thus, the present invention provides plants having modulated expression of a polypeptide that is substantially identical to a HAF, BEE1, and/or BEE3 polypeptide as described herein and having altered efficiency of fertilization, altered production of fruit in the absence of fertilization (i.e., parthenocarpy), and/or altered fruit size. The present invention further provides methods for altering the efficiency of fertilization, fruit production in the absence of fertilization (i.e., parthenocarpy), and/or fruit size in a plant by modulating the expression of a polypeptide that is substantially identical to a HAF, BEE1, and/or BEE3 polypeptide as described herein. The present invention still further provides for methods of generating such plants characterized by altered efficiency of fertilization, parthenocarpy, and/or fruit size.

II. HAF and BEE Polypeptides

In one aspect, the present invention provides for polypeptides that are substantially identical to HAF, BEE1, or BEE3 polypeptides as described herein and which modulate aspects of plant fertility, e.g., parthenocarpy, fertilization efficiency, and/or fruit size, when the level of expression of the polypeptide is modulated in a plant or a plant part, as compared to a plant lacking modulated expression of the polypeptide. In some embodiments, wherein the expression of the HAF or BEE polypeptide is increased or enhanced in the plant, the plant exhibits partenocarpy, has increased fertilization efficiency, and/or has increased fruit size as compared to a plant in which the level of expression of the HAF or BEE polypeptide is not increased or enhanced. In some embodiments, wherein the expression of the HAF or BEE polypeptide is decreased or inhibited in the plant, the plant has decreased fertilization efficiency, has decreased fruit size, and/or has decreased parthenocarpy as compared to a plant in which the level of expression of the HAF or BEE polypeptide is not decreased or inhibited.

HAF, BEE1, and BEE3 are structurally similar bHLH transcription factors. In *Arabidopsis*, HAF has 93% similarity to BEE1 within the bHLH protein subdomain, and HAF has 91% similarity to BEE3 within the bHLH protein subdomain. Thus, in some embodiments, a HAF or BEE polypeptide of the present invention is a polypeptide that is substantially identical to (e.g., is at least 70%, 75%, 80%, 85%, 90%, 91%, 92%, 93%, 94%, 95%, 96%, 97%, 98%, or 99% identical to) the bHLH protein subdomain (amino acid residues 115-161) of *Arabidopsis* HAF (SEQ ID NO:2), the bHLH protein subdomain (amino acid residues 155-202) of *Arabidopsis* BEE1 (SEQ ID NO:4), or the bHLH protein subdomain (amino acid residues 157-204) of *Arabidopsis* BEE3 (SEQ ID NO:6).

In some embodiments, a HAF or BEE polypeptide comprises SEQ ID NO:2, the *Arabidopsis* HAF protein sequence. In some embodiments, a HAF or BEE polypeptide comprises SEQ ID NO:4, the *Arabidopsis* BEE1 protein sequence. In some embodiments, a HAF or BEE polypeptide comprises SEQ ID NO:6, the *Arabidopsis* BEE3 protein sequence. Those of skill in the art will appreciate that variants of an *Arabidopsis* HAF or BEE protein sequence can be obtained by identifying additional HAF or BEE ortholog sequences from other plants or by generating directed or random mutations in the sequences. In some embodiments, a HAF or BEE polypeptide of the present invention is a polypeptide that is substantially identical to (e.g., at least 70%, 75%, 80%, 85%, 90%, 91%, 92%, 93%, 94%, 95%, 96%, 97%, 98%, or 99% identical to) any of SEQ ID NOs:2, 4, or 6. In some embodiments, a HAF or BEE polypeptide of the present invention is a polypeptide that is substantially identical to (e.g., at least 70%, 75%, 80%, 85%, 90%, 91%, 92%, 93%, 94%, 95%, 96%, 97%, 98%, or 99% identical to) any of SEQ ID NOs:2, 4, 6, 8, or 10.

III. Isolation of HAF and BEE Nucleic Acids

Embodiments of the present invention provide for the use of the above polypeptides and/or nucleic acid sequences encoding such polypeptides in the methods and compositions (e.g., expression cassettes, plants, etc.) of the present invention. In some embodiments, a nucleic acid sequence of the present invention comprises a polynucleotide encoding a HAF or BEE polypeptide that is substantially identical to (e.g., at least 70%, 75%, 80%, 85%, 90%, 91%, 92%, 93%, 94%, 95%, 96%, 97%, 98%, or 99% identical to) any of SEQ ID NOs:2, 4, 6, 8, or 10. In some embodiments, a nucleic acid sequence of the present invention comprises a polynucleotide encoding a HAF or BEE polypeptide comprising any of SEQ ID NOs:2, 4, 6, 8, or 10. In some embodiments, a polynucleotide of the present invention is substantially identical to (e.g., at least 70%, 75%, 80%, 85%, 90%, 91%, 92%, 93%, 94%, 95%, 96%, 97%, 98%, or 99% identical to) any of SEQ ID NOs:1, 3, 5, 7, or 9. In some embodiments, a polynucleotide of the present invention comprises any of SEQ ID NOs:1, 3, 5, 7, or 9. In some embodiments, a polynucleotide of the present invention is substantially identical to (e.g., at least 70%, 75%, 80%, 85%, 90%, 91%, 92%, 93%, 94%, 95%, 96%, 97%, 98%, or 99% identical to) a complement of any of SEQ ID NOs:1, 3, 5, 7, or 9.

The isolation of polynucleotides of the invention may be accomplished by a number of techniques. For instance, oligonucleotide probes based on the sequences disclosed here can be used to identify the desired polynucleotide in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon the sequence of a cloned HAF or BEE gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes such as HAF or BEE from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). The amplification conditions are typically as follows. Reaction components: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per ml Taq polymerase. Program: 96 C for 3 min., 30 cycles of 96 C for 45 sec., 50 C for 60 sec., 72 for 60 sec, followed by 72 C for 5 min.

Polynucleotides may also be synthesized by well-known techniques as described in the technical literature. See, e.g., Carruthers et al., Cold Spring Harbor Symp. *Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

IV. Use of HAF and BEE Nucleic Acids

In one aspect, the present invention provides methods of modulating fertility in a plant by introducing into a plant a recombinant expression cassette comprising a regulatory element (e.g., a promoter) operably linked to a HAF or BEE polynucleotide (e.g., a polynucleotide which when expressed in the plant modulates expression of a HAF or BEE polypeptide). The invention provides, for example, a transgenic plant characterized by having increased fertilization efficiency, increased fruit size, and/or parthenocarpy and having an expressed nucleic acid molecule encoding an HAF or BEE gene product, or fragment thereof, that is operatively linked to an exogenous constitutive regulatory element, thereby increasing expression of the HAF or BEE gene product. As another example, the invention provides a transgenic plant characterized by reduced fertility having an expressed nucleic acid molecule encoding an HAF or BEE gene product, or fragment thereof, or non-coding region, or antisense construct thereof, that is operatively linked to an exogenous constitutive regulatory element, thereby reducing endogenous expression (e.g., accumulation of expression products) of HAF or BEE genes.

As described below, the HAF or BEE sequences of the invention can be used to prepare expression cassettes useful in a number of techniques, including inhibiting, suppressing, or increasing expression or for ectopic expression.

A. Use of Nucleic Acids to Inhibit or Suppress Gene Expression

In one embodiment, the invention provides a transgenic plant that is characterized by reduced fertility (e.g., reduced fertilization efficiency, reduced fruit size, and/or lack of parthenocarpy) due to inhibition of expression of a nucleic acid molecule encoding a HAF or BEE polypeptide. In some embodiments, the transgenic plant has inhibited expression of polynucleotides encoding two or more HAF or BEE polypeptides, for example, inhibiting expression of HAF and BEE1, HAF and BEE3, or HAF, BEE1, and BEE3. In some embodiments, the transgenic plant has inhibited expression of a polynucleotide encoding a HAF or BEE polypeptide, wherein the transgenic plant comprises an otherwise wild-type background (e.g., the *Arabidopsis* Columbia ecotype) or a background that is otherwise wild-type with respect to genes relating to fertility characteristics. In still other embodiments, the transgenic plant has inhibited expression of a polynucleotide encoding a first HAF or BEE polypeptide, and further comprises a mutation in a coding sequence for another HAF or BEE polypeptide(s) (e.g., a RNA null allele).

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of HAF or BEE can be useful for producing a plant in which HAF or BEE expression is suppressed. The vectors of the present invention can be designed such that the inhibitory effect applies to other proteins within a family of genes exhibiting homology or substantial homology to the target gene. In some embodiments, the nucleic acid sequence comprises at least 20 contiguous nucleotides of an endogenous nucleic acid encoding a HAF or BEE polypeptide that is substantially (e.g., at least 70%, 75%, 80%, 85%, 90%, 91%, 92%, 93%, 94%, 95%, 96%, 97%, 98%, or 99%) identical or identical to SEQ ID NO:2, 4, 6, 8, or 10, or the complement thereof, such that expression of the polynucleotide inhibits expression of the endogenous HAF or BEE polypeptide. In some embodiments, the nucleic acid sequence comprises at least 20, at least 50, at least 75, at least 100, at least 125, at least 150, at least 175, at least 200 contingous nucleotides or more of any of SEQ ID NOs:1, 3, 5, 7, or 9, or a complement thereof.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of HAF or BEE genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is described in Haseloff et al., *Nature*, 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by means of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500, 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases. Thus, RNAi fragments may be selected for similarity or identity with the N terminal, C-terminal or middle region of the HAF or BEE sequences of the invention (i.e., those sequences lacking significant homology to sequences in the databases).

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

In some embodiments, inhibition of a HAF or BEE polypeptide is accomplished by means of introducing one or more genetic mutations in a nucleic acid sequence that codes for the HAF or BEE polypeptide. Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Genetic mutations can also be introduced, e.g., by introducing foreign DNA, such as T-DNA, into a gene of interest (e.g., HAF or BEE) in order to disrupt the expression or function of the gene.

B. Use of Nucleic Acids to Enhance Gene Expression

Isolated sequences prepared as described herein can also be used to prepare expression cassettes that enhance or increase endogenous HAF or BEE gene expression.

Overexpression of HAF or BEE is useful, for example, for generating plants characterized by parthencarpy, increased fertilization efficiency, and/or increased fruit size. Where overexpression of a gene is desired, the desired gene from a different species may be used to decrease potential sense suppression effects.

Any of a number of means well known in the art can be used to increase HAF or BEE activity in plants. Any organ can be targeted, such as shoot vegetative organs/structures (e.g. leaves, stems and tubers), roots, flowers and floral organs/structures (e.g. bracts, sepals, petals, stamens, carpels, anthers, and ovules), seed (including embryo, endosperm, and seed coat) and fruit. Alternatively, one or several HAF or BEE genes can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

V. Recombinant Expression Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al., *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the HAF or BEE gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide encoding a HAF or BEE polypeptide in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the IND1 gene are particularly useful for directing gene expression so that a desired gene product is located in the valve margin of fruit. Other suitable promoters include those from genes such as SHP1 or SHP2 (Savidge, B., Rounsley, S. D., and Yanofsky, M. F. (1995) *Plant Cell* 7: 721-733), or promoters from the HECATE genes (Gremski, K. et al., (2007) *Development* 134:3593-3601). Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

HAF or BEE nucleic acid sequences of the invention are expressed recombinantly in plant cells to enhance and increase levels of endogenous HAF or BEE polypeptides. Alternatively, antisense, sense suppression, siRNA, RNAi, or other HAF or BEE constructs (e.g., as described above) are used to suppress endogenous HAF or BEE levels of expression. A variety of different expression constructs, such as expression cassettes and vectors suitable for transformation of plant cells, can be prepared. Techniques for transforming a wide variety of higher plant species are well known and described in the technical and scientific literature. See, e.g., Weising et al. *Ann. Rev. Genet.* 22:421-477 (1988). A DNA sequence coding for a HAF or BEE polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

In some embodiments, the invention provides an HAF or BEE nucleic acid operably linked to a promoter capable of driving the transcription of the HAF or BEE coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. Typically, as discussed above, desired promoters are identified by analyzing the 5' sequences of a genomic clone corresponding to the HAF or BEE genes described here.

A. Constitutive Promoters

A promoter fragment can be employed which will direct expression of HAF or BEE nucleic acid in all transformed cells or tissues, e.g. as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a HAF or BEE polynucleotide (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.*

251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol* 208:551-565 (1989)), Gpc2 from maize (GenBank No. U45855, Manjunath et al., *Plant Mol. Biol.* 33:97-112 (1997)), or other transcription initiation regions from various plant genes known to those of skill. See also Holtorf *Plant Mol. Biol.* 29:637-646 (1995).

B. Inducible Promoters

Alternatively, a plant promoter may direct expression of the HAF or BEE nucleic acid of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897-909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. HAF or BEE coding sequences can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Other exemplary inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Roder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250: 533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)).

C. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Promoters from the HAF or BEE genes of the invention are particularly useful for tissue-specific direction of gene expression so that a desired gene product is generated only or preferentially in embryos or seeds, as described below.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistils, flowers, or any embryonic tissue. In some embodiments, the tissue-specific promoter is a reproductive tissue-specific promoter. Reproductive tissue-specific promoters may be, e.g., ovule-specific, embryo-specific, endosperm-specific, integument-specific, seed and seed coat-specific, pollen-specific, petal-specific, sepal-specific, or some combination thereof; as a non-limiting example, the reproductive tissue-specific promoter can be a promoter from a HECATE gene from *Arabidopsis* (Gremski et al. (2007) *Development* 3593-3601). In some embodiments, the tissue-specific promoter is a flower part-specific promoter, e.g., a promoter from the gene AGAMOUS from *Arabidopsis* (Bowman et al. (1991) *Plant Cell* 3:749-758). In some embodiments, the tissue-specific promoter is an epidermal-specific promoter, e.g., a promoter from the gene MERISTEM LAYER 1 from *Arabidopsis* (AtML1) (Sessions et al. (1999) *The Plant Journal* 20:259-263; Sessions et al. (2000) *Science's STKE* 289:779).

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol.* 22:10131-1038); vivparous-1 from *Arabidopsis* (Genbank No. U93215); atmyc1 from *Arabidopsis* (Urao (1996) *Plant Mol. Biol.* 32:571-57; Conceicao (1994) *Plant* 5:493-505); napA from *Brassica napus* (GenBank No. J02798, Josefsson (1987) JBL 26:12196-1301); and the napin gene family from *Brassica napus* (Sjodahl (1995) *Planta* 197:264-271).

One of skill in the art will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the HAF or BEE polynucleotide is expressed through a transposable element. This allows for constitutive, yet periodic and infrequent expression of the polypeptide encoded by the HAF or BEE polynucleotide. The invention also provides for use of tissue-specific promoters derived from viruses including, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

VI. Production of Transgenic Plants

In another aspect, the present invention provides for the production of transgenic plants having modulated expression of a polypeptide substantially identical to SEQ ID NO:2, 4, 6, 8, or 10, wherein the plant exhibits one or more modulated fertility characteristics. In some embodiments, the present invention provides for the production of transgenic plants having increased expression of a polypeptide that is identical to or substantially identical to SEQ ID NO:2, 4, 6, 8, or 10, and characterized by having increased fertilization efficiency, increased fruit size, and/or parthenocarpy, wherein the plant comprises a heterologous expression cassette for expressing a HAR or BEE coding sequence as described herein. In some embodiments, the present invention provides for the production of transgenic plants having decreased expression of a polypeptide that is identical to or substantially identical to SEQ ID NO:2, 4, 6, 8, or 10, and characterized by having decreased fertilization efficiency, decreased fruit size, and/or lack of parthenocarpy, wherein the plant comprises a polynucleotide sequence that inhibits the expression of a HAR or BEE polypeptide, as described herein. In some embodiments, a transgenic plant is generated that contains a complete or partial sequence of a polynucleotide that is derived from a species other than the species of the transgenic plant. It should be recognized that transgenic plants encompass the plant or plant cell in which the recombinant polynucleotide sequence is introduced as well as progeny of such plants or plant cells that contain the recombinant polynucleotide sequence, including the progeny that have the recombinant polynucleotide stably integrated in a chromosome.

DNA constructs of the invention (e.g., a recombinant expression cassette comprising a HAF or BEE coding sequence driven by a heterologous promoter, or a recombinant expression cassette comprising a polynucleotide sequence that inhibits expression of a HAF or BEE polypeptide driven by a heterologous promoter) may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium* tumefaciens host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the DNA construct (e.g., a recombinant expression cassette as described herein) is stably incorporated in transgenic plants and confirms to be operable, it can be introduced into other plants by sexual crossing. Any of a number of standard breeding techniques can be used, depending upon the species to be crossed.

The methods described herein (e.g., for increasing expression of a HAF or BEE polypeptide or inhibiting expression of a HAF or BEE polypeptide) can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and *Zea*. In some embodiments, the plant is a vegetable- or fruit-producing plant. In some embodiments, the plant is a plant of the genus *Solanum*. In some embodiments, the plant is a plant of the genus *Vitis*. In some embodiments, the plant is a plant of the genus *Citrus*.

Those of skill will recognize that a number of plant species can be used as models to predict the phenotypic effects of transgene expression in other plants. For example, it is well recognized that both tobacco (Nicotiana) and *Arabidopsis* plants are useful models of transgene expression, particularly in other dicots.

VII. Selecting for Plants with One or More Modulated Fertility Characteristics

Plants having one one or more characteristics of modulated fertility (e.g., increased or decreased fertilization efficiency, increased or decreased parthenocarpy, and/or increased or decreased fruit size) can be selected in many ways. One of ordinary skill in the art will recognize that the following methods are but a few of the possibilities.

One method of selecting plants with modulated fertility characteristics is to determine the number of fertilized siliques per plant produced by a pollinated transgenic plant as compared to a non-transgenic control plant, wherein an increased number of fertilized siliques per plant produced by the transgenic plant as compared to the control plant indicates increased fertilization efficiency in the transgenic plant as compared to the control plant, and wherein a decreased number of fertilized siliques per plant produced by the transgenic plant as compared to the control plant indicates decreased fertilization efficiency in the transgenic plant as compared to the control plant. For example, in some embodiments, a transgenic plant (e.g., a plant having an increased level of expression of a HAF or BEE polypeptide, e.g., a plant having an increased level of expression of a polypeptide that is substantially identical to any of SEQ ID NOs:2, 4, 6, 8, or 10) has increased fertilization efficiency as compared to a non-transgenic control plant when the transgenic plant produces at least about 10%, at least 15%, at least 20%, at least 25%, at least 30%, at least 40%, at least 50%, at least 60%, at least 70%, at least 80%, at least 90%, or more fertilized siliques per plant as compared to the control plant. In other embodiments, a transgenic plant (e.g., a plant having a decreased level of expression of a HAF or BEE polypeptide, e.g., a plant having a decreased level of expression of a polypeptide that is substantially identical to any of SEQ ID NOs:2, 4, 6, 8, or 10) has decreased fertilization efficiency as compared to a non-transgenic control plant when the transgenic plant produces about 90%, 80%, 70%, 60%, 50%, 40%, 30%, 20%, 10%, or less fertilized siliques per plant as compared to the control plant.

In another method, transgenic plants can be selected that have modulated efficiency of fertilization under sub-optimal conditions, for example but not limited to, high or low temperature or high humidity conditions. Determinination of whether the transgenic plant has increased or decreased fertilization efficiency under sub-optimal conditions as compared to a non-transgenic control plant can be measured, e.g., as described above.

In another method, transgenic plants can be selected that exhibit parthenocarpy (fruit production without pollination). For example, in some embodiments, a transgenic plant (e.g., a plant having an increased level of expression of a HAF or BEE polypeptide, e.g., a plant having an increased level of expression of a polypeptide that is substantially identical to any of SEQ ID NOs:2, 4, 6, 8, or 10) exhibits parthenocarpy when the average length of a silique produced by an emasculated transgenic plant is at least about 10%, at least 15%, at least 20%, at least 25%, at least 30%, at least 40%, at least 50%, at least 60%, at least 70%, at least 80%, or at least 90% longer than the average length of a silique produced by an emasculated non-transgenic control plant.

In still another method, transgenic plants can be selected that have modulated fruit yield, e.g., increased fruit size and/or increased numbers of fruits produced. In some embodiments, a transgenic plant (e.g., a plant having an increased level of expression of a HAF or BEE polypeptide, e.g., a plant having an increased level of expression of a polypeptide that is substantially identical to any of SEQ ID NOs:2, 4, 6, 8, or 10) has increased fruit yield as compared to a non-transgenic control plant when the average size of a fruit produced by the transgenic plant is at least about 10%, at least 15%, at least 20%, at least 25%, at least 30%, at least 40%, at least 50%, at least 60%, at least 70%, at least 80%, or at least 90% larger than the average size of a fruit produced by the control plant.

EXAMPLES

Here we report the identification of the HALF FILLED (HAF) gene, a bHLH-encoding transcription factor required for reproductive tract development. We show that HAF acts redundantly with two closely related genes, BRASSINOSTEROID ENHANCED EXPRESSION1 (BEE1) and BEE3. All three genes are expressed in an overlapping pattern during reproductive tract development and contribute jointly to ECM production and programmed cell death. In haf bee1 bee3 triple mutants, extracellular matrix formation and cell death fail to occur within the transmitting tract, and a haf bee1 bee3 triple mutant drastically reduces the efficiency of pollen tube growth throughout the reproductive tract. We also investigated the genetic interactions of HAF, BEE1 and BEE3 with other transcription factors involved in reproductive tract development. Finally, we used loss-of-function and misexpression studies to explore the role of HAF in regulating reproductive tract development and growth. Using a minimal pollination assay, we show that HAF is necessary and sufficient to promote fertilization efficiency. Our studies further show that HAF expression depends on the NTT gene and on an auxin signaling pathway mediated by the ARF6, ARF8 and HEC genes.

Materials and Methods

Plants

All wild-type plants used in this study were in the Columbia background. For all phenotypic analyses and in situ hybridization experiments, *Arabidopsis thaliana* seeds were stratified for 3 to 5 days at 4° C. after sowing. Plants were grown at 22 to 24° C. under long-day (LD) conditions. The haf_mutant, CSHL ET2536, has an insertion into the third exon and is a RNA null allele. It was obtained from the Cold Spring Harbor collection in the Ler background and was backcrossed into the Columbia background. The bee1, bee3, ntt-1, arf6-2, arf8-3, hec1, and hec3 mutants were previously published (Crawford, B. C. et al., *Curr Biol* 17:1101-8 (2007); Friedrichsen, D. M. et al., *Genetics* 162:1445-56 (2002); Gremski, K. et al., *Development* 134:3593-601 (2007); Ichihashi, Y. et al., *Plant and Cell Physiology* 51:252-261 (2010); Nagpal, P. et al., *Development* 132:4107-18 (2005)). The hec2 allele, SM.17339, was crossed into the hec1 and hec3 mutants. Seed numbers for different genotypes were determined by counting the number of seeds in each silique after the fifth silique produced. Infertile siliques and siliques containing less than 10 seeds were excluded. The statistical significance of the difference in seed number was analyzed using the student's t-test.

Genotyping and Overexpression Lines

All primers used in this study are listed in Table 1, infra. To genotype haf we used HAF7x and HAF8x. HAF8x was used along with the Ds3-2 primer to detect the insertion. HAF corresponds to AT1G25330. The HAF cDNA was subcloned behind an operator array in BJ36 plasmid to generate responder lines (Moore, I. et al., *Proceedings of the National Academy of Sciences of the United States of America* 95:376-381 (1998)) using HAFPOP1+ and HAFPOP1− and transformed into *Arabidopsis* using the pGREEN0029 binary plasmid.

In Situ RNA Hybridization, Microscopy, and Histology

In situ hybridization was carried out as described previously (Long et al. 1996) with the following modifications. Tissue samples were fixed in FAA for 2.5 hours at room temperature and slides were not treated with RNase. Substrate solution for alkaline phosphatase color reaction was prepared using 2% of a NBT/BCIP stock solution (Roche Diagnostic, Germany) in 100 mM Tris pH 9.5, 100 mM NaCl, 50 mM MgCl2.

The HAF probe was transcribed using T7 RNA polymerase (Promega) from a PCR product produced from a PCR 3.1 vector using M13 forward and reverse primers. An HAF cDNA clone was obtained by PCR amplification of cDNA obtained from stage 12 carpels using the primers HAFCDNA+ and HAFCDNA− and cloned into the PCR 3.1 vector.

Embedding of plant material in JB-4 media, sectioning, and alcian blue staining of thin sections was performed as previously described (Crawford, B. C. et al., *Curr Biol* 17:1101-8 (2007)). Paraplast sections were embedded as previously described (Roeder, A. H. et al., *Curr Biol* 13:1630-5 (2003)). Samples were sectioned to 8 μm with a disposable steel blade on a Jung Biocut microtome and mounted on slides. Slides were dewaxed in three changes for 10 minutes each of Histoclear and mounted with permount.

Minimal Pollinations, Aniline Blue Staining, and Carpel Measurements

Aniline blue staining of pollen tubes in pistils was performed as described by (Jiang, L. et al., *Plant Cell* 17:584-96 (2005)). The flowers were emasculated at stage 12 and left for 24 hours. For the time series we added maximal pollen with a paintbrush. The pollinated pistils were collected after 2, 6 and 24 hours. For the qrt pollinations we used a fine hair to pick up a single pollen cluster from a slide under a compound microscope. The pollen cluster was then transferred to the stigma under a dissecting microscope. We then waited 14 days for the seeds to set and used imageJ to analyze the lengths of carpels (Abramoff, M. et al., *Biophotonics Int* 11:36-42 (2004); Rasband, W., ImageJ, US National Institutes of Health, Bethesda, Md., USA, http.rsb.info.nih.gov/ij (1997)).

GUS Staining

We used pollen containing the ACAS:: GUS construct (Schiott, M. et al., *Proc Natl Acad Sci USA* 101:9502-7 (2004)). We created the HAF::GUS, BEE1:: GUS and BEE1:: GUS constructs using the PD137 vector with the primers in Table 1 to amplify 3191 bp, 1384 bp and 2635 bp regions of the HAF, BEE1 and BEE3 promoters, respectively (Blazquez, M. A. et al., *Development* (Cambridge) 124:3835-3844 (1997)). The flowers were emasculated at stage 12 and pollen was added after 24 hours. GUS staining of tissue sections was as previously described (Dinneny, J. R. et al., *Development* 133:1645-55 (2006)).

Results

Phenotype of HALF FILLED (HAF)

Figure 10:
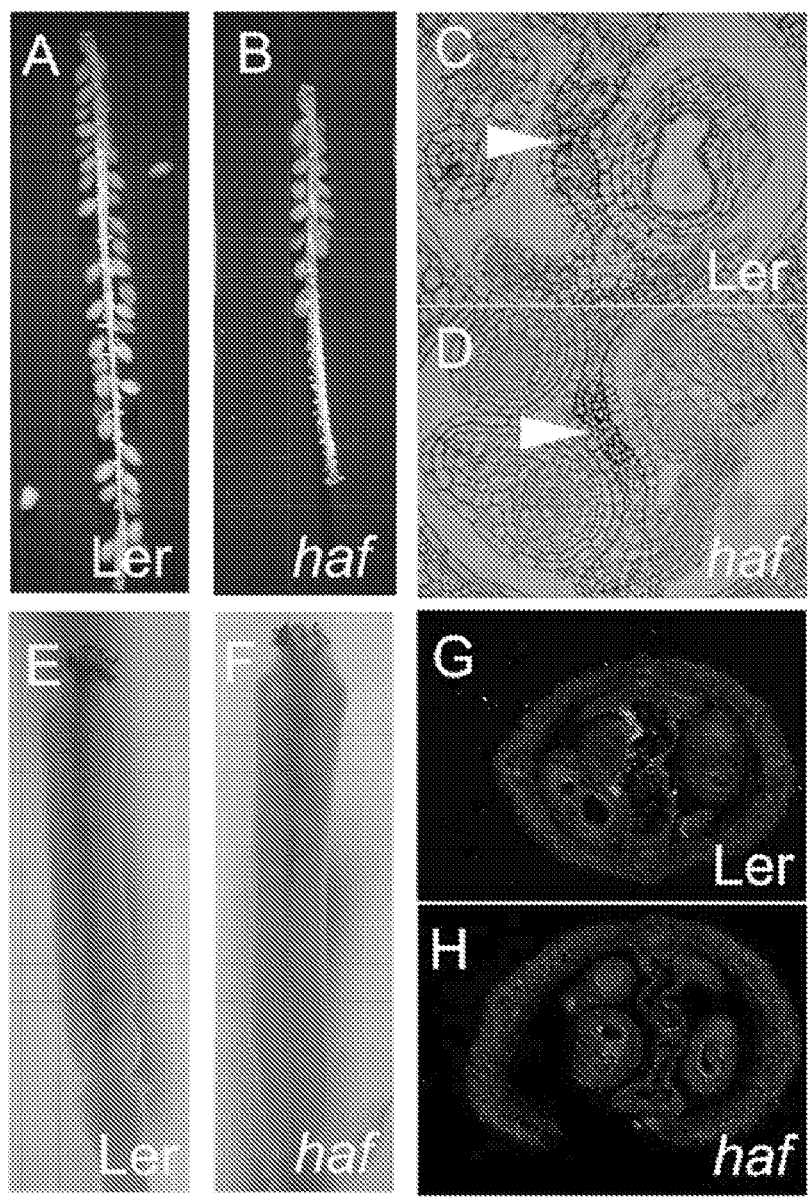
FIG. 10. The haf single mutant phenotype in the Landsberg erecta background. (A,B) Siliques with valves removed to show seed set. (C,D) Sections stained with alcian blue and neutral red were taken from Ler wild type (C) and haf mutant (D). Arrowheads indicate loss of alcian blue staining in haf mutant. (E-H) Distribution of pollen tubes visualized with GUS labeled pollen in whole mount (E,F), and transverse sections (G,H) 24 hours after pollination in Ler (E,G) and haf mutant (F,H), as shown by GUS labeled pollen tubes. The cross sections were taken from the middle of the gynoecium.

In the Landsberg erecta ecotype, fruit of half filled (haf) mutants are smaller than wild-type and contain few seeds that are preferentially localized to the upper portion of the fruit (FIG. 10A, B). To determine if these defects are female-specific, we pollinated wild-type carpels with haf-mutant pollen and found that a normal seed set resulted. Conversely, when we pollinated haf-mutant carpels with wild-type pollen, the haf mutant phenotype was observed, indicating that the haf phenotype is female-specific. Surprisingly, when the haf allele was introgressed into the Columbia (Col) ecotype, siliques had restored fertility. This suggests that one or more genes act redundantly with HAF in the Col ecotype and that these genes are either not present, or not functional, in the Ler ecotype.

HAF is predicted to encode a 223-amino-acid protein with similarities to basic helix-loop-helix (bHLH) transcription factors. It is grouped within a subfamily of bHLH genes containing 16 members (Friedrichsen, D. M. et al., *Genetics* 162:1445-56 (2002)), and is structurally most similar to two that have previously been characterized, BEE1 and BEE3 (Friedrichsen, D. M. et al., *Genetics* 162:1445-56 (2002)). These latter two genes, along with a third less closely-related member, BEE2, were initially identified as responding to exogenous application of brassinosteroid (BR). However, unlike BEE1, BEE2 and BEE3, HAF was not found to be activated by application of BR in seedlings (Friedrichsen, D. M. et al., *Genetics* 162:1445-56 (2002)). Within the bHLH protein subdomain, HAF (bHLH No. 75) has 93% similarity to BEE1 (bHLH No. 44) and 91% similarity to BEE3 (bHLH No. 50), and the three genes have identical intron-exon structures. The bee1 bee3 double mutant was reported to have normal levels of fertility (Friedrichsen, D. M. et al., *Genetics* 162:1445-56 (2002)). To test for genetic redundancy with HAF, we generated different mutant combinations of haf, bee1 and bee3. Whereas the haf single mutant produced the same number of seeds as wild type, the haf bee1 double mutant produced an average of only 27.3 seeds per silique (n=46), compared with 51.4 seeds per silique in wild type (n=16). The haf bee1 bee3 triple mutant (labeled hbb in FIG.s) had the most severe effect on fertility, yielding an average of only 22.3 seeds per silique (n=60) (compared with haf bee1 p<0.001). In both haf combinations, seeds were produced predominantly in the apical part of the silique (FIG. 1). As our previous work involving NTT was done in the Columbia ecotype, and since the haf bee1 bee3 mutant had the most severe fertility defect, we used this genotype for the remainder of our analyses.

The haf bee1 bee3 mutant phenotype is very similar to that of ntt (Crawford, B. C. et al., *Curr Biol* 17:1101-8 (2007)). In both cases, seed production is reduced relative to wild type, the seeds are largely localized to the upper portion of the fruit, and the phenotype is female-specific. Genetic studies have shown NTT to be required for proper formation of the transmitting tract. To better understand the relationship between ntt, haf, bee1, and bee3, we generated multiple mutants. Whereas the ntt single mutant produced an average of 20.4 seeds per silique (n=57), the ntt haf double mutant produced an average of only 14.9 seeds (n=56). The most severe effect on seed number was found in the ntt haf bee1 bee3 quadruple mutant, which produced an average of only 13.5 seeds produced per silique (n=39) (compared with ntt haf p=0.017).

HAF, BEE1, and BEE3 Expression

Figure 2:
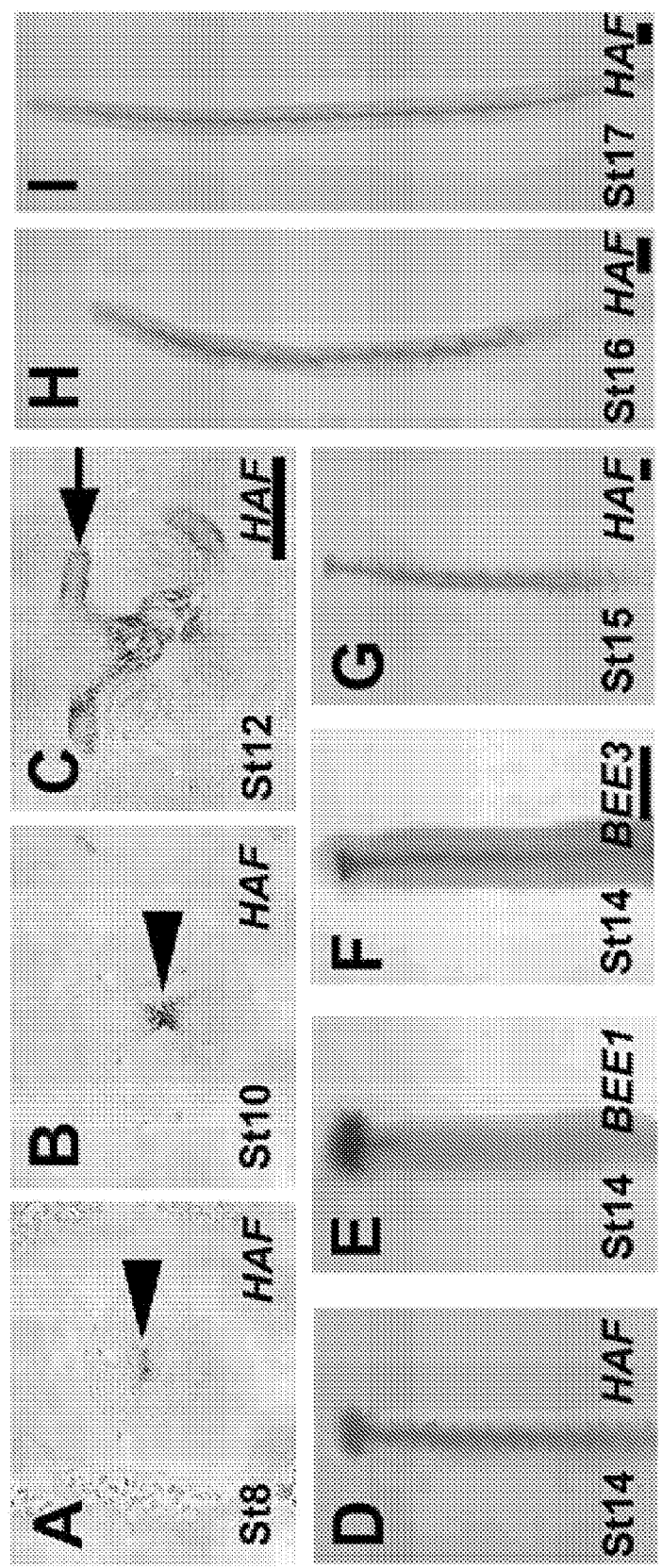
FIG. 2. HAF, BEE1 and BEE3 expression in developing wild-type carpels. (A-C) Tranverse sections of stage 8 (A), stage 10 (B), and stage 12 (C) wild-type carpels probed with HAF by in situ hybridization. Arrowheads indicate position of HAF expression. Arrow indicates epidermal expression in funiculus. (D-I) Beta-glucoronidase (GUS) staining on whole-mount carpels and fruits with HAF::GUS at stage 14 (D), stage 15 (G), stage 16 (H) and stage 17 (I). Stage 14 BEE1::GUS (E) and BEE3::GUS staining (F). Scale bars are 50 p.m.

To investigate how HAF, BEE1 and BEE3 function in reproductive tract development, we analyzed their expression patterns using both RNA in situ hybridization and beta-glucuronidase (GUS) reporter gene constructs. HAF was expressed throughout the reproductive tract during stages 8 to 15 of flower development, whereas BEE1 and BEE3 showed more restricted patterns of expression (FIG. 2).

Figure 11:
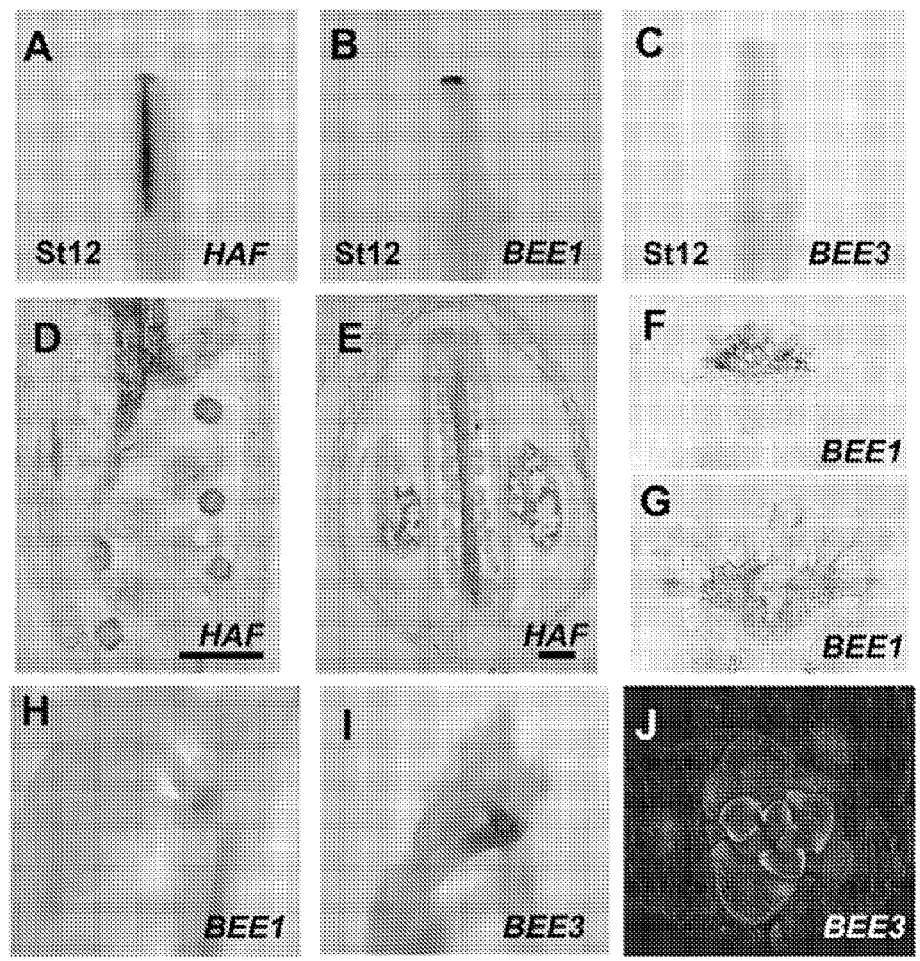
FIG. 11. GUS staining of HAF, BEE1 and BEE3 promoters in different plant stages and tissues. (A-C, H-J) Beta-glucoronidase (GUS) staining on stage 12 carpels (A-C) and vegetative meristems (H-J) using HAF::GUS (A), BEE1::GUS (B,H), and BEE3::GUS (C,I, J). Tranverse sections of wild-type vegetative meristem (J). (D-E) Longtitudinal sections of wild-type carpels probed with HAF by in situ hybridization. (F,G) Longtitudinal sections of wild-type carpels stage 12 (F) and stage 14 (G) probed with BEE1 by in situ hybridization. Scale bars are 100 µm.

Expression of HAF was first observed by RNA in situ hybridization during stage 8 of gynoecium development, in the medial ridges of the septum, which at this time have grown together and fused (arrowhead in FIG. 2A) (Bowman, J. L., *Arabidopsis*: An Atlas of Morphology and Development, New York: Springer-Verlag New York, Inc. (1993)). By stage 10, HAF expression was observed in the center of the septum where the transmitting tract arises (arrowhead in FIG. 2B). Expression had expanded to include both the septum transmitting tract and funiculus (arrow in FIG. 2C) by pre-fertilization stage 12. Expression in the funiculus was predominantly in the epidermis (arrow in FIG. 2C; FIG. 11).

To compare HAF, BEE1 and BEE3 expression patterns, we made GUS constructs driven by their respective promoters. Fertilization of the carpel occurs during stage 13 and the HAF promoter was seen to be active before and after this stage in the stigma, style, transmitting tract and funiculus (FIG. 2D). The BEE1 promoter was active in the stigma and the top of the style, while the BEE3 promoter was active in the transmitting tract and style, albeit at a lower level compared with HAF (FIG. 2E, F). The expression of BEE1 within the carpel was confirmed by in situ hybridization (FIG. 11). BEE1 and BEE3 therefore have restricted, overlapping expression patterns with HAF within the reproductive tract.

In later stages of fruit development after fertilization, HAF expression is maintained in the style, transmitting tract and funiculus and only diminishes during late maturation at stage 17 (FIGS. 2G, H and I). HAF is expressed exclusively in the developing carpel according to our results and publically available microarrays (Atgenexpress), but BEE1 and BEE3 are expressed more widely. The promoter-GUS constructs for BEE1 and BEE3 show expression in other parts of the plant, including vegetative tissues (FIG. 11). However, no obvious aberrant phenotype was observed in any of these tissues in the haf bee1 bee3 triple mutant.

Pollen Tube Growth in the Haf; Bee1; Bee3 Triple Mutant

Pollen tubes grow basally from the stigma through the different tissues of the reproductive tract to reach ovules. Since HAF, BEE1 and BEE3 are expressed in reproductive tract tissues, it seemed likely that at least part of the phenotype of haf bee1 bee3 might be due to impaired pollen tube growth. We therefore used aniline blue staining to reveal callose, a component of the pollen tube cell wall, to visualize pollen tubes in the carpel. We analyzed the extent of tube growth in both Col and the triple mutant at 2, 6 and 24 hours post-fertilization. The first unopened flower was emasculated and grown for 24 hours to allow full development of the reproductive tract before being maximally pollinated with wild type pollen and then fixed at the indicated times.

At 2 hours, pollen germination and/or stylar passage were already seen to be impaired in the triple mutant. The width of the stylar pollen tube pathway (arrowheads in FIGS. 3A and B) was 88.3+/−9.7 um (n=11) for Col, and in the haf bee1 bee3 triple mutant it was only 55.2+/−8.8 um (n=13) (p<0.001). Although fewer pollen tubes entered the upper ovary chamber, their extent of ingress was roughly similar to that of wild type. The farthest extent of apical-basal pollen tube growth into the carpel at this time point was 0.66+/−0.07 mm (n=11) in wild type compared with 0.58+/−0.11 mm (n=13) in haf bee1 bee3 (FIG. 3B).

Figure 3:
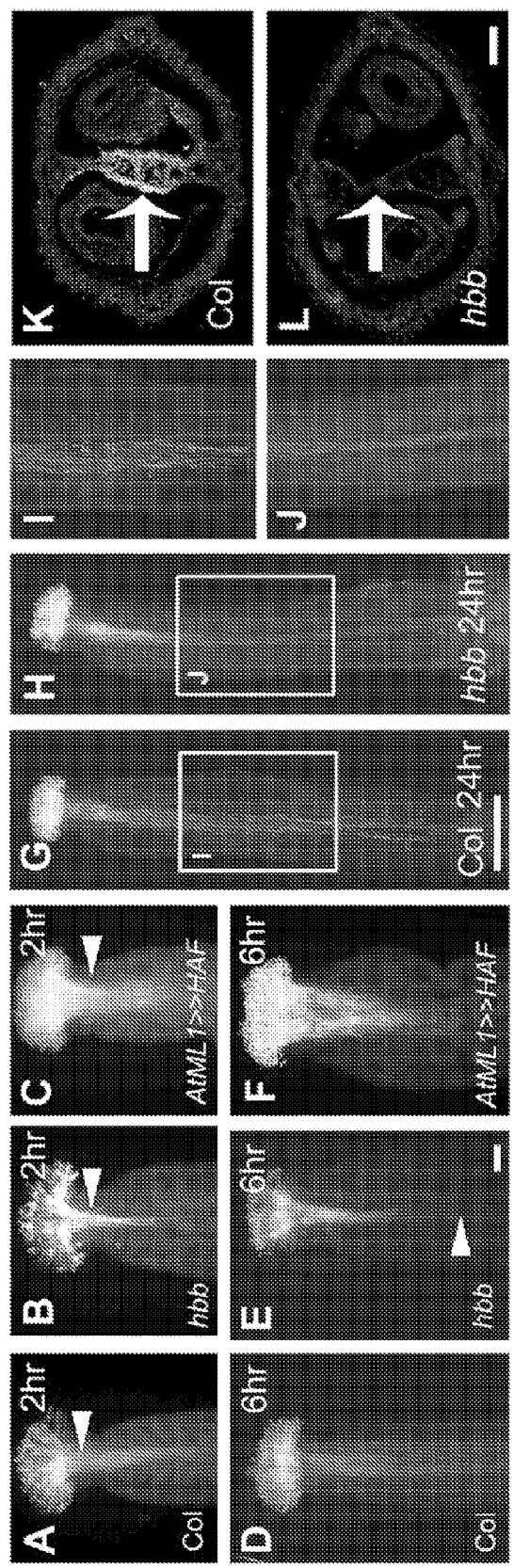
FIG. 3. Pollen tube growth in wild type, haf bee1 bee3 (hbb) mutant and AtML1>>HAF. (A-J) Pollen tube growth stained with aniline blue of wild type (A,D,G,I), haf bee1 bee3 mutant (B,E,H,J), and AtML1>>HAF (C,F) 2 hrs post pollination (A-C), 6 hrs post pollination (D-F) and 24 hours post pollination (G-J). (I, J) Close ups of regions indicated by boxes in (G) and (H). (K,L) Distribution of pollen tubes visualized with GUS labeled pollen (Schiott, M. et al., *Proc Natl Acad Sci USA* 101:9502-7 (2004)). Transverse sections were taken 24 hours after pollination and processed after an additional 24 hours in wild type (K) and haf bee1 bee3 mutant (L). The cross sections were taken from the middle of the carpel. Scale bars are 50 µm.

The effect on apical-basal pollen tube growth was much more pronounced at 6 hours (compare FIGS. 3D and E). Pollen tubes were found throughout the transmitting tract in wild type, but had significantly less apical-basal and lateral growth in haf bee1 bee3 where they were funneled into a narrow path down the center of the transmitting tract (arrowhead in FIG. 3E).

At 24 hours, pollen tubes had reached the base of carpels in wild type, but had only grown half the length of the carpels in the mutant (FIG. 3G, H). Moreover, pollen tubes were restricted to a smaller and smaller region of growth within the transmitting tract (compare FIG. 3I, J).

Figure 12:
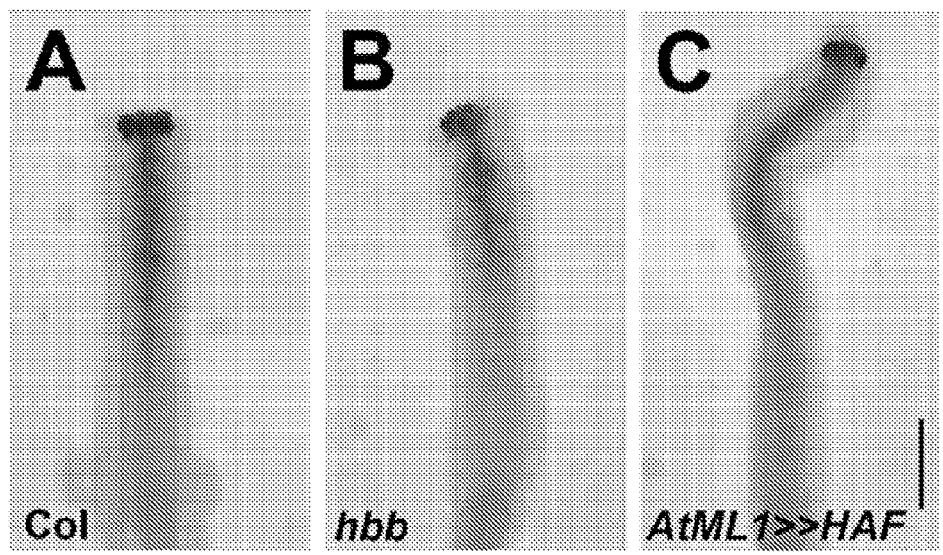
FIG. 12. GUS stained pollen tube growth in Col, haf bee1 bee3 triple mutant, and AtML1>>HAF carpels. (A-C) Distribution of pollen tubes in Col (A), haf bee1 bee3 triple mutant (B), and AtML1>>HAF (C) visualized with GUS labeled pollen in whole mount 24 hours after pollination. Scale bars are 100 µm.

Whole mount analysis of carpels displaying pollen-specific GUS expression 24 hr after pollination was consistent with results from aniline blue staining (FIG. 12A, B). Cross-sections at the mid-point of the carpels confirmed that in contrast to the widespread distribution of pollen tubes in wild type, pollen tubes in the triple mutant were constrained to a very small region within the transmitting tract (compare arrows in FIG. 3K, L).

Transmitting Tract Structure in Haf Bee1 Bee3 Mutants

We undertook a detailed morphological analysis of the transmitting tract in haf bee1 bee3 triple mutant plants. To visualize transmitting tract tissue in the triple mutant, carpels were thin-sectioned and stained with alcian blue to reveal acidic polysaccharides, major components of the extra cellular matrix (ECM) of the transmitting tract. Neutral red was used as a counterstain to highlight cell walls. Sections were obtained from stages 12 (pre-anthesis), 14 (post-anthesis) and 17 (mature fruit) of wild type and haf bee1 bee3.

Figure 4:
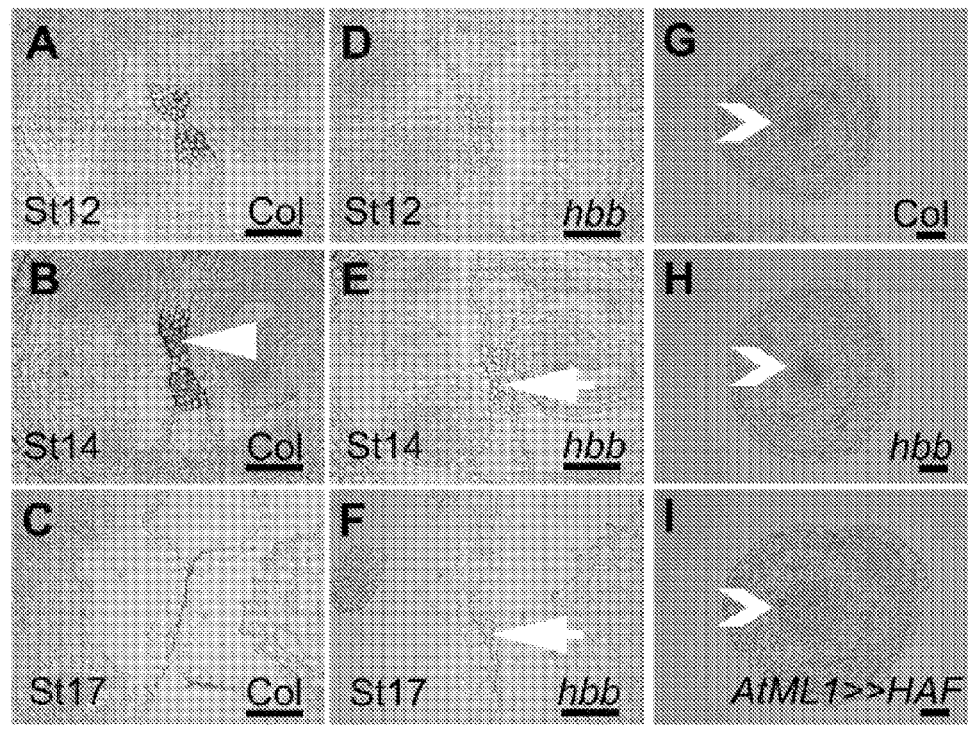
FIG. 4. Transverse sections of different stages of transmitting tract development. (A-I) Sections stained with alcian blue and neutral red were taken from wild type (A-C and G), haf bee1 bee3 (hbb) mutant (D-F) and (H) and AtML1>>HAF (I) at stage 12 (A,D), stage 14 (B,E, G-I), and stage 17 (C,F) style region. Arrowhead (B) indicates cell breakdown in wild type. Arrow in (E) and (F) indicates cells intact in haf bee1 bee3 mutant. Chevron (G-I) indicates position of style transmitting tract. Scale bars are 100 µm.

At stage 12, the wild-type transmitting tract region stained strongly with alcian blue indicating the presence of ECM (FIG. 4A). In haf bee1 bee3 mutants, the region of septum corresponding to the transmitting tract septum appeared cytologically normal, but stained only slightly (FIG. 4D), indicating severely reduced ECM production. Immediately after fertilization at stage 14, wild type cells within the transmitting tract undergo increased cell death and stain intensely for alician blue (arrowhead in FIG. 4 B) (Crawford, B. C. et al., Curr Biol 17:1101-8 (2007)). At this stage in the triple mutant, there was only a minimal increase in the very low level of alcian blue staining seen at stage 12, and there was still no indication of cell death (Arrow FIG. 4E). In the mature wild type silique at stage 17, all cells between the septum epidermal layers were absent, leaving a two cell-layered structure (FIG. 4C) (Crawford, B. C. et al., Curr Biol 17:1101-8 (2007)). In the triple mutant, residual cells could still be seen between the epidermal cell layers (arrow in FIG. 4F)

We also examined transmitting tract structure in the style of haf bee1 bee3. In wild type, the stylar transmitting tract consisted of tightly packed smaller cells, the majority of which stained for ECM (FIG. 4G), whereas in the triple mutant, the width of tightly packed cells in the style was significantly reduced, and relatively few showed evidence of alcian blue ECM staining (compare chevron in FIGS. 4G and H).

Ectopic Expression of HAF Promotes Both Pollen and Carpel Growth

Figure 13:
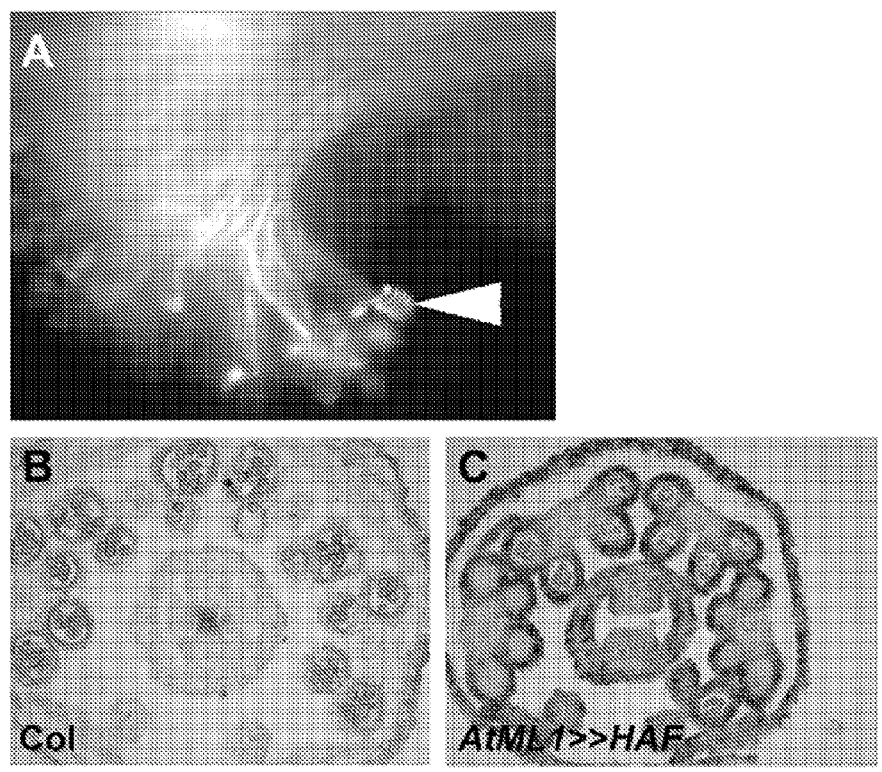
FIG. 13. Phenotype and expression analysis of AtML1>>HAF. (A) Pollen tubes visualized with aniline blue stain in AtML1>>HAF. Arrowhead indicates strange pollen tube growth on stigmatic papillae. (B,C) Tranverse sections of wild-type stage ten flowers probed with HAF by in situ hybridization of Col (B) and AtML1>>HAF (C).

Loss-of-function studies have demonstrated that HAF is required for efficient fertilization and plays an important role in development of the reproductive tract. In order to determine if HAF is sufficient to produce phenotypes when ectopically expressed, we initially tried to express HAF from the "constitutive" CaMV35S promoter. However, we were unable to recover transgenic plants, as tested by in situ hybridization, that misexpressed HAF, suggesting that constitutive misexpression may be lethal. To circumvent this problem, we expressed HAF from the epidermal-specific AtML1 promoter ("AtML1>>HAF") (FIG. 13)(Sessions, A. et al., The Plant Journal 20:259-263 (1999); Sessions, A. et al., Science's STKE 289:779 (2000)). A number of transcription factors have been misexpressed from the AtML1 promoter, often leading to non-autonomous effects in internal tissues (Savaldi-Goldstein, S. et al., Nature (London) 446: 199-202 (2007).; Sessions, A. et al., Science's STKE 289: 779 (2000)).

We first investigated the effect of AtML1>>HAF on growth of unfertilized carpels and fertilized fruit. The most striking growth phenotype of ectopic AtML1>>HAF expression was an increased size and bent morphology for AtML1>>HAF carpels. Similar phenotypes were also observed when HAF was expressed under the control of the AGAMOUS promoter (data not shown). To quantify the effect of HAF on carpel growth, we measured carpel length one day (1 dpe) and seven days (7 dpe) after flower emasculation in wild type, haf bee1 bee3, and AtML1>>HAF. Emasculation was used to prevent the dramatic increase in carpel size resulting from fertilization. At 1 dpe, there was no difference between wild type 1.65+/−0.15 mm (n=10) and haf bee1 bee3 triple mutant carpels 1.65+/−0.17 mm (n=10) (FIG. 5A, B). In contrast, the AtML1>>HAF carpels were significantly larger, 1.82+/−

Figure 5:
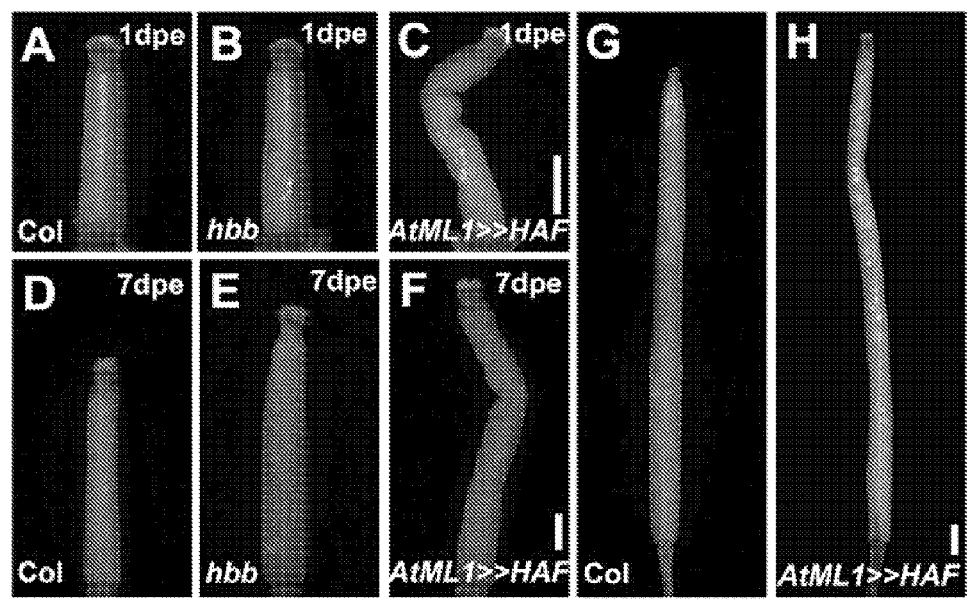
FIG. 5. Growth in emasculated carpels and fruit of haf bee1 bee3 mutant and AtML1>>HAF. (A-F) Emasculated carpels of wild type (A,D), haf bee1 bee3 mutant (B,E) and AtML1>>HAF (C,F) left for one day (A-C) and seven days (D-F). (G-H) Examples of wild type (G) and AtML1>>HAF (H) fruits. dpe: days post emasculation, hbb: haf bee1 bee3 mutant. Scale bars are 500 µm.
Figure 8:
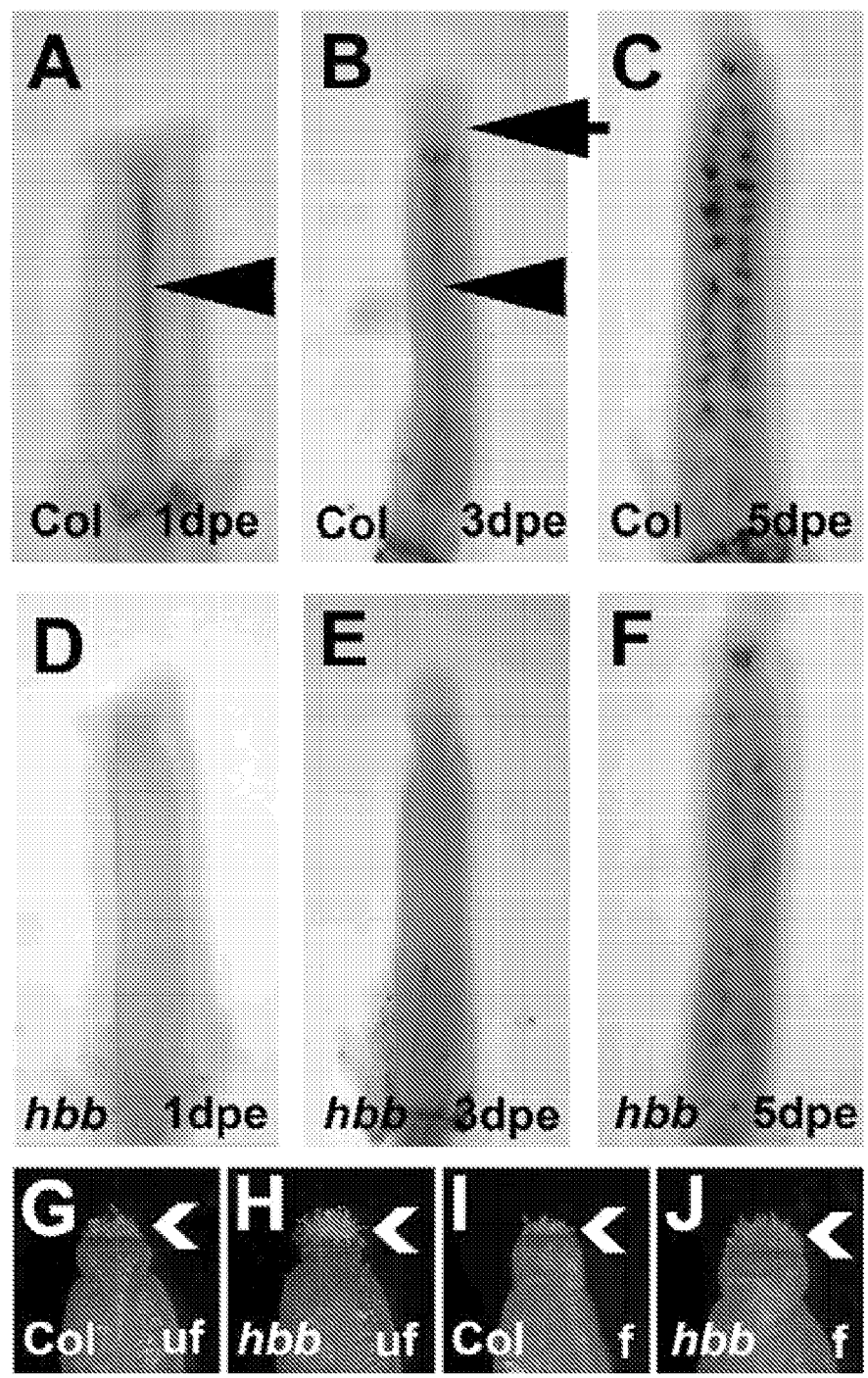
FIG. 8. BFN1::GUS staining and stigma cell death phenotype in wild type and haf bee1 bee3 mutant. (A-F) BFN1::GUS staining of emasculated carpels of wild type (A-C) and haf bee1 bee3 mutant (D-F) at one (A,D), three (B,E), and five days (C,F) post emasculation. Arrowheads indicate staining in the transmitting tract; arrow indicates staining in the stigma. (G-J) Stigma structure in unfertilized (G,H) and fertilized (I,J) in carpels seven days after emasculation of wild type (G,I) and haf bee1 bee3 mutant (H,J). Chevron indicates stigma. dpe: days post emasculation, hbb: haf bee1 bee3 mutant, uf: unfertilized, f: fertilized.
Figure 9:
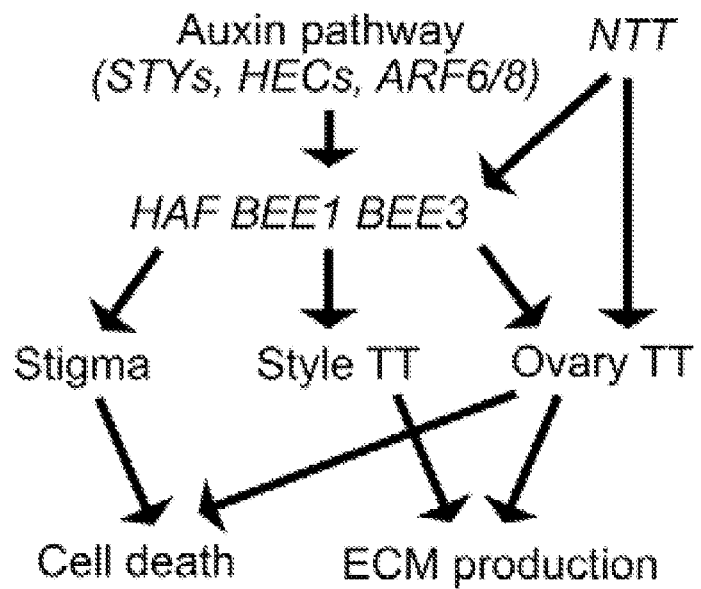
FIG. 9. Genetic network controlling HAF expression and reproductive tract development. The STYs, HECs and ARFs mediate different aspects of the auxin signaling pathway to positively regulate HAF expression in combination with NTT. HAF, BEE1 and BEE3 promote ECM production in the style and ovary transmitting tract along with cell death in the stigma and ovary transmitting tract. NTT also controls cell death and ECM production in the ovary transmitting tract.

0.21 mm (n=17) with a characteristic bent morphology (compared with wt p=0.037)(FIG. 5C). By 7 dpe, wild-type carpels had grown slightly even though they had not been pollinated, reaching 3.25+/−0.22 mm (n=12). In the haf bee1 bee3 triple mutant, carpels were noticeably bigger than wild type, averaging 3.71+/−0.26 mm (n=10)(compared with wt p<0.001) (FIGS. 5 D and E). The largest carpels were produced by the AtML1>>HAF genotype, 4.49+/−0.46 mm (n=17)(compared with wt p<0.001) and these again had a bent morphology (FIG. 8F). These data show that misexpression of HAF is sufficient to promote substantial overgrowth in unfertilized carpels, but that such growth is uncoordinated and leads to distortions in carpel shape.

We next tested how ectopic HAF expression influenced the final size of fertilized fruit. Wild type and AtML1>>HAF flowers were emasculated and carpels maximally pollinated with wild type pollen and the length of the resultant fruit was measured after 7 days. AtML1>>HAF siliques measured on average 14.3+/−2.9 mm (n=44), and were larger than wild-type siliques, 12.0+1-1.6 mm (n=55) (p<0.001) (FIGS. 5G and H). The increased silique size was due to an increased number of cells in the silique, since the average valve cell length in wild type, 0.243+/−0.045 mm (n=49), was comparable to that in AtML1>>HAF, 0.239+/−0.046 mm (n=43). The overall number of seeds remained the same but when the internal septum of AtML1>>HAF was compared to wild type, there was more space between seeds along the septum. The increased septum size could be one cause of the bent morphology observed in the AtML1>>HAF carpels. Interestingly, the fertilized AtML1>>HAF fruit (H) were much straighter than those unfertilized carpels (C). We excluded haf bee1 bee3 triple mutants from these studies as the reduction in seed number of this genotype leads to smaller fruit regardless of any effect on growth.

Since the most striking phenotype of the haf bee1 bee3 triple mutant is a lack of proper transmitting tract development and an impairment of pollen tube growth, we examined these features in AtML1>>HAF carpels. Aniline blue staining was used to monitor pollen tube growth at both 2 and 6 hours after pollinating emasculated flowers. There was a significant increase in the number of pollen tubes in AtML1>>HAF carpels compared with wild type at both time points (arrowheads in FIG. 3A,C,D,F). At 2 hours (FIGS. 3A and C), the average width of the pollen tube pathway in the style was 88.3+/−9.7 um (n=11) in wild type, and was 111.7+/−22.7 um (n=15) in AtML1>>HAF (p<0.01). The farthest extent of apical-basal pollen tube growth into the carpel was 0.66+/−0.07 mm (n=11) in wild type, and 0.75+/−0.1 mm (n=15) in AtML1>>HAF (p=0.013). At 6 hours, pollen tubes appeared more widespread in the style in AtML1>>HAF compared with wild type while the extent of the pollen tubes within the ovary transmitting tract was similar (compare FIGS. 3D and F). Pollen tube growth is thus significantly enhanced in the AtML1>>HAF reproductive tract.

HAF Controls Efficiency of Fertilization

Whereas impaired pollen tube growth in haf bee1 bee3 carpels implies that basal ovules are less likely to be fertilized, it was unclear how the enhanced pollen tube growth seen in AtML1>>HAF carpels might influence fertility. To quantify how the fertilization efficiency is affected in the different genotypes, we performed minimal pollinations on carpels from emasculated carpels using quartet (qrt) mutant pollen (Preuss, D. et al., Science (Washington D.C.) 264:1458-1460 (1994)). In the qrt mutant, pollen grains fail to separate in the final stage of pollen development, leaving a characteristic four pollen grain bundle. During fertilization, the pollen grains separate and act independently. This allowed us to add an exact number of pollen grains and measure how many fertilized siliques were produced by each pollination event.

We placed one of these qrt bundles on the stigma of wild type (n=97), or haf bee1 bee3 (n=63) and AtML1>>HAF (n=85). In wild type, 33% of carpels were fertilized, compared with only 8% of carpels in the haf bee1 bee3 triple mutant and 49% of AtML1>>HAF carpels. An average of 0.54 (sem=0.09) seeds were produced per carpel in wild type compared with 0.91 (sem=0.12) seeds in AtML1>>HAF carpels (p=0.015). This indicates that the ability of ovules to be fertilized is reduced in the triple mutant and significantly increased in the AtML1>>HAF genotype.

HAF Acts Downstream of the NTT and HEC Genes

Figure 14:
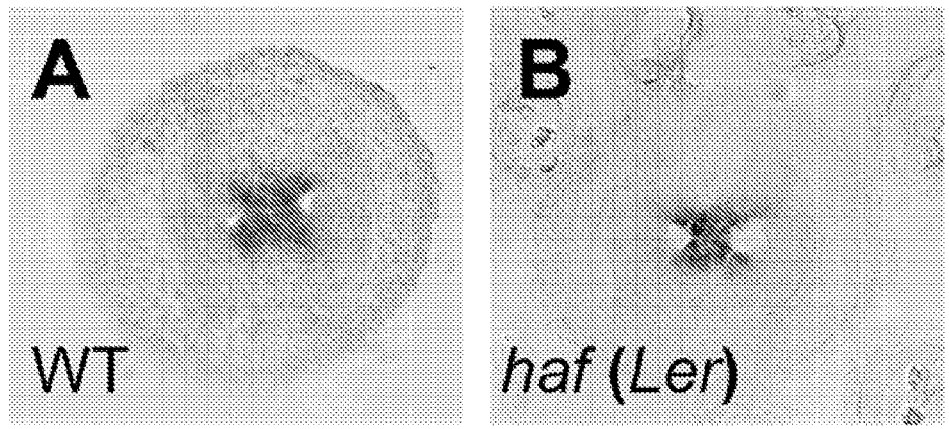
FIG. 14. Expression of NTT in wild type and haf single mutant. (A,B) in situ hybridization of Stage 10 carpels probed with NTT in Landsberg erecta (A) and haf single mutant (B). Scale bars are 50 µm.

Previous studies have shown that the transmitting tract does not develop correctly in the ntt mutant, causing very inefficient pollen tube growth (Crawford, B. C. et al., Curr Biol 17:1101-8 (2007)). The fertility defects of haf bee1 bee3 triple mutants are very similar to those of nu, and HAF expression in the septum of stage 9 to 12 carpels overlaps with that of NTT (FIG. 2A-C) (Crawford, B. C. et al., Curr Biol 17:1101-8 (2007)). This suggests that HAF and NTT could act in the same pathway to promote reproductive tract development. To check this, we analyzed HAF expression in ntt carpels using the HAF:: GUS construct. HAF:: GUS expression was greatly reduced at both stage 12 and stage 14 in ntt mutant carpels (Compare FIGS. 6A and C, B and D). In contrast, no change was seen for NTT expression in haf mutant carpels, as determined by in situ hybridization (FIG. 14). These data suggest that NTT acts upstream to promote HAF expression in the transmitting tract.

Since expression of HAF is partially dependent on NTT, we wanted to determine if misexpression of HAF could rescue the ntt mutant phenotypes. To test this, we introduced the AtML1>>HAF transgene into ntt and examined pollen growth by aniline blue staining. Both ntt and ntt AtML1>>HAF flowers were emasculated and the carpels maximally hand-pollinated with wild type pollen before staining 6 hours later with aniline blue. In ntt, pollen tubes passed normally through the style but were severely inhibited upon reaching the ovary transmitting tract (compare FIGS. 6K and L), as previously reported (Crawford, B. C. et al., Curr Biol 17:1101-8 (2007)). In ntt AtML1>>HAF, pollen tubes still had great difficulty entering the ovary transmitting tract, but the extent of basal pollen tube growth was modestly increased compared with ntt (arrowhead FIG. 6L). Expression of HAF from AtML1>>HAF therefore does partially rescue ntt pollen tube growth. However, since the number of seeds produced by ntt AtML1>>HAF carpels was the same as for ntt (data not shown), this improvement in pollen tube growth was not sufficient to rescue fertility.

The hec1 hec3 double mutant shows a significant loss of reproductive tract tissue and a corresponding reduction in fertility (Gremski, K. et al., Development 134:3593-601 (2007)). It is therefore not surprising that we found HAF:: GUS expression to be dramatically reduced in the hec1 hec3 double mutant (compare FIGS. 6A and B with E and F). These data suggest that HEC acts upstream of HAF to promote reproductive tract development.

Figure 6:
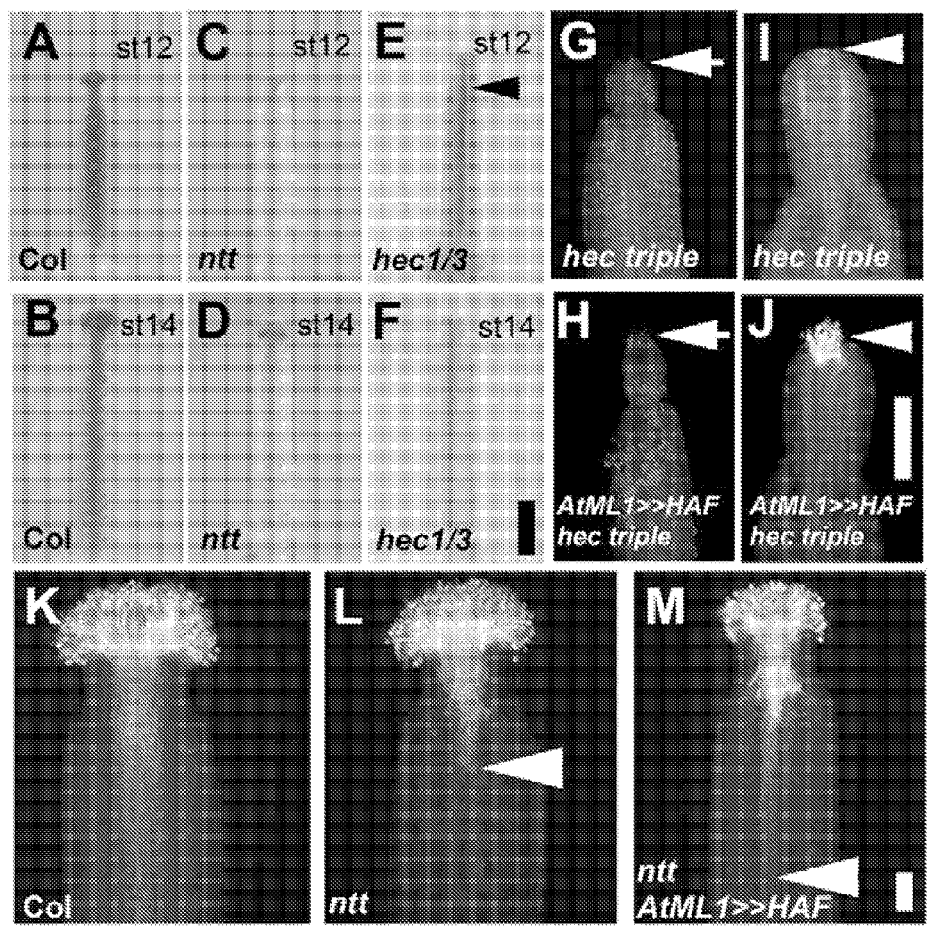
FIG. 6. Genetic relationship between HAF and NTT and HECs. (A-F) HAF:: GUS staining in wild type (A,B), ntt (C,D) and hec1 hec3 (E,F) carpels at stages 12 (A,C,E) and 14 (B,D,F). Arrowhead indicates low level staining (E). (G-H) Stigma and style of hec1 hec2 hec3 triple mutant (G) and hec1 hec2 hec3 triple mutant with AtML1>>HAF (H). Arrow indicates stigmatic tissue or lack of stigmatic tissue. (I-J) Aniline blue staining of pollen tube growth blue fixed at 24 hours post pollination in carpels in hec1 hec2 hec3 triple mutant (I) and hec1 hec2 hec3 triple mutant with AtML1>>HAF (J). Arrowhead indicates pollination or lack of pollination. (K-M) Pollen tube growth stained with aniline blue fixed at 24 hours post pollination in carpels of wild type (K) ntt (L), and ntt AtML1>>HAF (M). Arrowheads indicate extent of pollen tube growth. Scale bars are 500 µm (A-J) and 100 µm (K-M).

Previous work had determined that removing the activity of all three hec genes caused complete loss of reproductive tract tissue (Gremski, K. et al., Development 134:3593-601 (2007)). This phenotype was obtained using a combination of hec1 hec3 insertional mutants along with RNAi to target HEC2. We obtained an insertion mutation in hec2 and created a hec1 hec2 hec3 triple mutant that confirmed the complete loss of reproductive tract tissue phenotype (FIG. 6G). Consistent with previous work, the hec1 hec2 hec3 mutant cannot be pollinated as no stigmatic tissue is produced. Interestingly, misexpression of HAF through AtML1>>HAF is sufficient to restore some stigmatic tissue to the hec1 hec2 hec3 mutant carpels (compare FIGS. 6G and H). As a result of this stigmatic tissue it is possible to pollinate the AtML1>>HAF hec1 hec2 hec3 carpels (FIGS. 6I and J). A limited number of seeds can be produced from AtML1>>HAF hec1 hec2 hec3 carpels compared with the complete infertility of hec1 hec2 hec3 triple mutants.

ARF6 and ARF8 Control Reproductive Tract Development and are Positive Regulators of HAF Expression ARF8 is a member of a transcription factor family that activates or represses gene expression in response to auxin. The first mutant allele of ARF8 to be characterized was called fruit without fertilization (renamed arf8-4) (Vivian-Smith, A. et al., *Development* 128: 2321-31 (2001)). The arf8-4 mutant allele has a fertility phenotype similar to both ntt single mutants and haf bee1 bee3 triple mutants (Goetz, M. et al., *Plant Physiol* 145:351-66 (2007); Goetz, M. et al., *Plant Cell* 18:1873-86 (2006); Vivian-Smith, A. et al., *Development* 128: 2321-31 (2001)). Subsequent analysis of ARF8 revealed that it acts redundantly with AUXIN RESPONSE FACTOR 6 (ARF6). These two closely related transcription factors control maturation and development of the carpel (Nagpal, P. et al., *Development* 132:4107-18 (2005); Wu, M. F. et al., *Development* 133:4211-8 (2006)). Because ARF6 and ARF8 are both expressed in a pattern that resembles HAF expression (Wu, M. F. et al., *Development* 133:4211-8 (2006)), we analyzed HAF expression in arf6 single and arf6 arf8 double mutants to see if these ARF genes play a role in regulating HAF.

Figure 7:
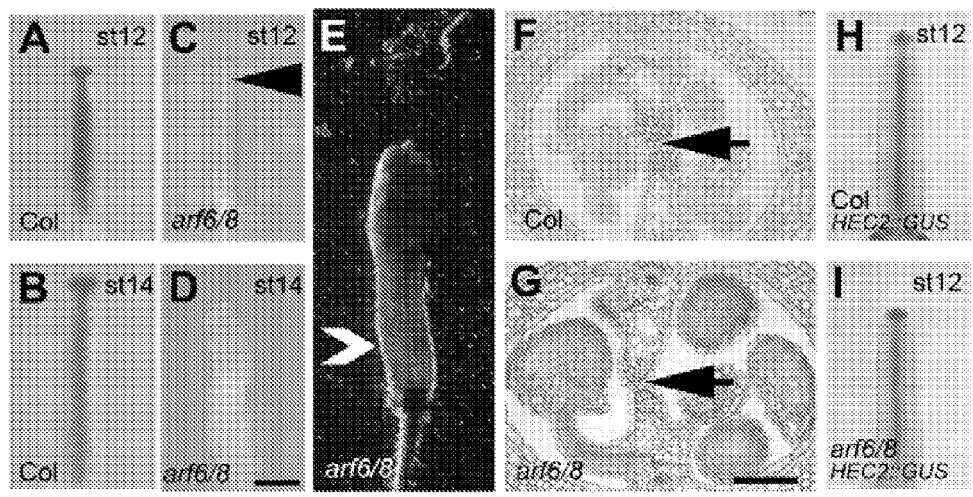
FIG. 7. Relationship between HAF, ARF6, ARF8 and HEC2. (A-D) HAF:: GUS staining in wild type (A,B) and arf6 arf8 (C,D) at stages 12 (A,C) and 14 (B,D). Arrowhead indicates low level staining (C). (E) Hand pollinated and fertilized fruit of arf6 arf8 mutant, chevron indicates the loss of basal seed. (F,G) Transverse sections stained with alcian blue and neutral red of wild type (F) and arf6 arf8 mutant (G) stage 12 carpels. Arrow indicates transmitting tract. (H,I) HEC2::GUS staining in stage 12 of wild type (H) and arf6 arf8 (I). Scale bars are 500 µm (A-D, H,I). Scale bars are 50 µm (F,G).

HAF::GUS expression was severely reduced in the arf6 arf8 double mutant, showing only faint expression in the style and transmitting tract (compare FIGS. 7A and C, arrowhead indicates expression). We also compared HAF expression in stage 14 wild type carpels with a carpel from an equivalent position from the arf6 arf8 double mutant. HAF::GUS expression was almost completely absent in the arf6 arf8 mutant at this stage (compare FIGS. 7B and D). Although arf6 arf8 mutants show some loss of transmitting tract tissue which will reduce HAF expression for trivial reasons, most of the effect observed in FIG. 7 appears due to impaired regulation. Indeed, in contrast to the loss of HAF expression, the HEC2 expression is unaffected in arf6 arf8 double mutants as shown by the HEC2::GUS construct (FIGS. 7H and I) (Gremski, K. et al., *Development* 134: 3593-601 (2007)). To determine if ARF6/ARF8 expression is independent of HAF, we analyzed ARF8 expression in haf bee1 bee3 using the gARF8::GUS construct (Wu, M. F. et al., *Development* 133:4211-8 (2006) and found no reduction in gARF8::GUS expression (data not shown). Taken together, these data suggest that ARF6 and ARF8 act upstream of HAF, but not the HECs, in control of reproductive tract development.

Carpels of the arf6 arf8 double mutant arrest development at stage 12 and do not undergo anthesis, preventing self fertilization. After hand pollination, pollen tubes grew aberrantly within arf6 arf8 double mutant carpels, suggesting a defect in reproductive tract development (Wu, M. F. et al., *Development* 133:4211-8 (2006)). To investigate this further, we performed fertility and morphological studies with arf6 arf8 mutants.

Fertility was examined in the arf6 arf8 double mutant by applying wild-type pollen to arf6 arf8 carpels and examining seed distribution after 2 weeks. An average of only 7.8 seeds per fruit (n=11) were produced from mutant plants, compared with 50 seeds for wild type. The fertility of arf6 arf8 mutant carpels was quite variable, with one carpel of the 11 pollinated producing 25 seeds. The seeds were smaller than those of wild type and the resulting fruit lacked structures characteristic of a wild-type silique, such as a valve margin. Seeds were always found apically within the carpel, similar to haf bee1 bee3 mutants (chevron in FIG. 7E).

We created a haf bee1 bee3 arf6 arf8 quintuple mutant to see if haf bee1 bee3 could enhance the fertility defect of arf6 arf8. Carpels of the quintuple mutant could still be pollinated to produce an average of 6.1 seeds per fruit (n=10) and the maximum number of seeds obtained from an individual carpel was 12. Since the fertility of haf bee1 bee3 arf6 arf8 was equivalent to that of arf6 arf8, these data are consistent with the idea that ARF6 and ARF8 act upstream of HAF, BEE1, and BEE3.

Figure 15:
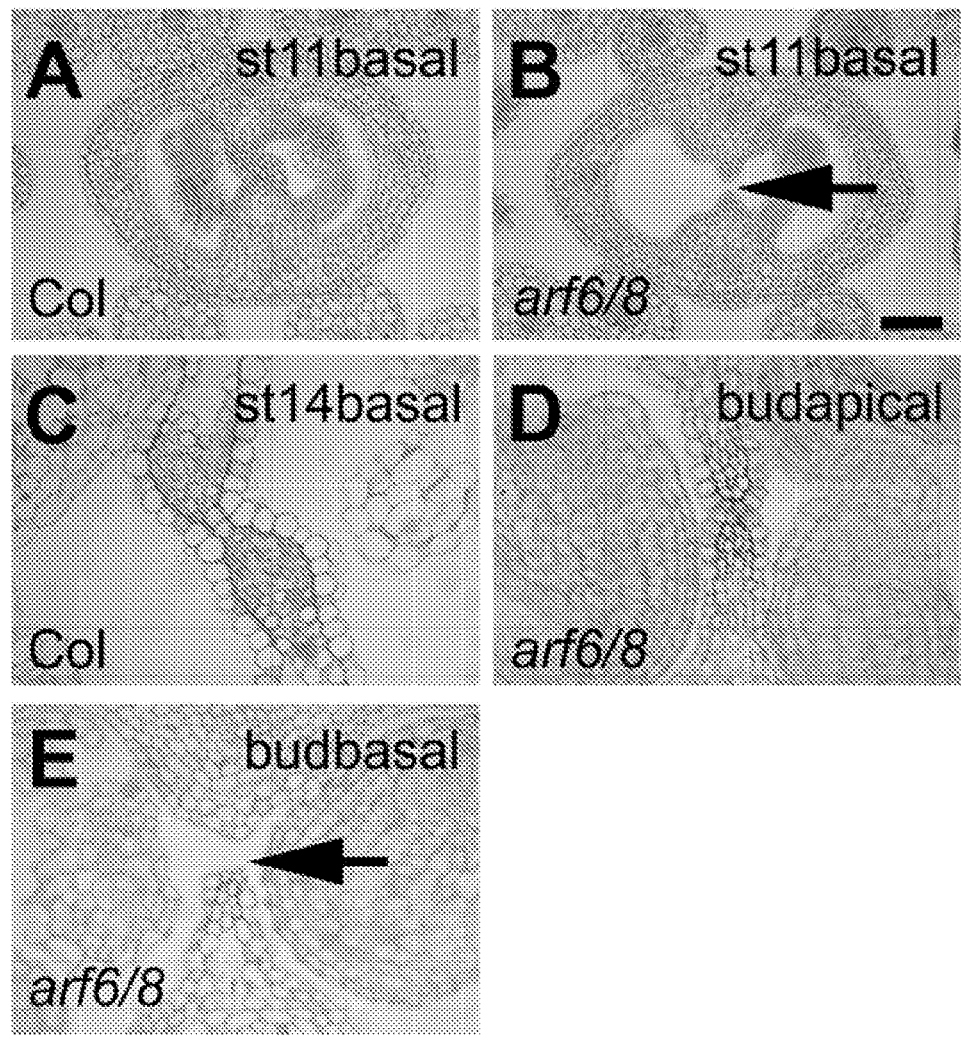
FIG. 15. Transverse sections of different stages of transmitting tract development. (A-E) Sections stained with alcian blue and neutral red were taken from stages 11 (A,B) and 14 (C) and equivalent stage of arf6 arf8 (D,E) were used. Sections were taken from basal region (A-C,E) of gynoecium and apical region of carpel (D). Arrow indicates lack of carpel fusion in basal region of gynoecium in arf6 arf8. Scale bars are 50 μm.

Transmitting tract structure was examined in arf6 arf8 carpels using thin cross sections of stage 12 carpels stained with alcian blue. We chose to perform the comparison at stage 12 since arf6 arf8 carpels stop development at this stage. ECM production was found to be substantially reduced in the septum of arf6 arf8 (compare arrows in FIG. 7F, G). The reduction in ECM staining supports the idea that ARF6 and ARF8 act in the same pathway as HAF, BEE1, and BEE3 to promote reproductive tract development. An additional growth-related phenotype in the arf6 arf8 reproductive tract was a failure of the septum to fuse completely in the basal region of the carpel (FIG. 15) indicating that ARF6 and ARF8 are thus also involved in promoting generalized growth of the septum. There was no noticeable rescue of the arf6 arf8 double mutant by the AtML1>>HAF construct. This is not surprising considering the wide role ARF6 and ARF8 play in overall flower and fruit development.

HAF Controls Cell Death within the Reproductive Tract

Cell death in the ovary transmitting tract is necessary for efficient pollen tube growth (Crawford, B. C. et al., *Curr Biol* 17:1101-8 (2007)). Disintegrative cell death is initiated prior to fertilization and is potentiated by the arrival of pollen. In contrast to wild type, cells in the transmitting tract of developing haf bee1 bee3 triple mutants remain intact before and after fertilization, suggesting that HAF, BEE1, and BEE3 function in promoting cell death. To examine this further, we used the BIFUNCTIONAL NUCLEASE1 (BFN1) (Farage-Barhom, S. et al., *J Exp Bot* 59:3247-58 (2008)) gene as a marker since it is normally expressed in tissues undergoing cell death, including the transmitting tract (Farage-Barhom, S. et al., *J Exp Bot* 59:3247-58 (2008)). Expression from a BFN1::GUS reporter was examined in unfertilized haf bee1 bee3 carpels at 1, 3, and 5 days post-emasculation.

In wild type, BFN1::GUS was strongly expressed in the ovary transmitting tract at both 1 and 3 dpe (days post emasculation) (arrowhead in FIG. 8A, B). Faint expression was also seen in the stigma at 3 dpe (arrow in FIG. 8B), suggesting that stigmatic papillae also undergo cell death in the absence of pollination, similar to cells in the ovary transmitting tract. BFN1::GUS was expressed strongly in ovules 5 dpe, showing that ovules abort around this time (FIG. 8C). In contrast to wild type, no GUS expression was detected in the haf bee1 bee3 mutant in the ovary transmitting tract at either 1 or 3 dpe (FIG. 8D, E), and expression was also absent from the stigma at 3 dpe (FIG. 8E). However, ovule expression was the same as in wild type and was clearly observed 5 dpe (FIG. 8F).

It is interesting that haf bee1 bee3 stigmata never showed any evidence of BFN1::GUS expression. We examined this in more detail by examining the structural integrity of wild type and mutant stigma for both fertilized and unfertilized carpels up to 7 days after emasculation. Consistent with a lack of BFN1::GUS expression, mutant stigma (FIG. 8H, J) remained intact longer than did wild type stigma (FIG. 8G, I) under both conditions.

It seemed possible that delayed cell death in mutant stigmata might prolong pollen receptivity (Carbonell-Bejerano, P. et al., *Plant Physiol* 154:163-72 (2010)). Wild-type carpels have been reported to be receptive to pollination and fertilization for up to four days after the flower has opened at anthesis (Vivian-Smith, A. et al., *Development* 128: 2321-31 (2001)). To test this, we emasculated wild type and haf bee1 bee3 flowers and maximally pollinated carpels over a period of 7 days. We found that both wild-type and mutant carpels could only be fertilized for up to four days post emasculation. Further, aniline blue staining showed no pollen grain germination in either wild type or mutant beyond 4 days-post-emasculation. It therefore appears that stigmatic cell death does not determine how long carpels remain receptive for fertilization.

Discussion

Genetic Redundancy of HAF, BEE1, and BEE3

In the Columbia ecotype, haf single mutants resemble wild-type plants. However, when mutations in HAF are combined with mutations in BEE1 and BEE3, the resulting triple mutants display dramatic defects in reproductive tract formation. HAF, BEE1 and BEE3, which share more than 90% sequence similarity within the bHLH domain and identical intron/exon structures, are the three most closely related members of a 16 member subfamily of bHLH transcription factors. Not only are HAF, BEE1 and BEE3 closely related, but they also share overlapping expression patterns in the female reproductive tract. The previous observation that BEE1 and BEE3 have redundant roles in brassinosteroid signaling (Friedrichsen, D. M. et al., *Genetics* 162:1445-56 (2002)) raises the intriguing possibility that brassinosteroids could play a role in reproductive tract formation. Interestingly, haf single mutants display a dramatic fruit phenotype in the Ler background, indicating that the BEE1 and BEE3 genes are unable to substitute for HAF in this ecotype. To circumvent the complexities of the ecotype and functional redundancy, we carried out most of our studies in the Columbia background using the haf bee1 bee3 triple mutant.

The expression patterns of HAF, BEE1 and BEE3 within the reproductive tract suggest that each gene has a subtly different function. Whereas HAF is expressed in all the tissues of the reproductive tract, BEE1 is expressed only in the stigma and stylar transmitting tract, and BEE3 is expressed only in the ovary transmitting tract. The more widespread expression of HAF could explain why both the haf bee1 and haf bee3 double mutants both show reduced fertility, whereas the bee1 bee3 double mutant does not.

Previous work demonstrated that BEE1 and BEE3 share functionally redundancy in the brassinosteroid signaling pathway with BEE2, a more distantly related member of the bHLH transcription factor family (Friedrichsen, D. M. et al., *Genetics* 162:1445-56 (2002)). Although no expression studies were previously reported for BEE1 and BEE3, our analyses show that these genes are expressed in vegetative tissues. It will be interesting to determine the expression patterns of all members of this sub-family of bHLH genes to identify additional candidates for functional redundancy. Our observation that ectopic expression of HAF leads to a variety of effects on the overall architecture of the plant suggests that other members of this sub-family of genes likely have significant roles during plant development.

Genes Controlling Transmitting Tract Development

The transmitting tract begins at the boundary between the stigma and style and extends through the style and to the base of the ovary. Within the style, the HAF, BEE1 and BEE3 genes play important roles as evidenced by the restricted pollen tube growth and dramatically reduced ECM production in haf bee1 bee3 mutants. Moreover, ectopic HAF expression increases transmitting tract tissues within the style, leading to a corresponding increase in the number of pollen tubes passing through this region. In contrast, the NTT gene does not appear to play a role within the stylar transmitting tract and there is no restriction on pollen tube movement through this region of ntt mutants.

HAF, BEE1 and BEE3 are also important for normal development of the ovary transmitting tract, and in haf bee1 bee3 mutants, ECM production in this region is severely reduced. Moreover, the cell breakdown leading to cell death that normally occurs in this region, which has been linked to components of the ECM (Crawford, B. C. et al., *Curr Biol* 17:1101-8 (2007); Crawford, B. C. and Yanofsky, M. F., *Curr Biol* 18:R972-8 (2008); Gao, M. and Showalter, A. M., *Plant J* 19:321-31 (1999); Wu, H. and Cheung, A., *Plant Molecular Biology* 44:267-281 (2000)), fails to occur normally in haf bee1 bee3 mutants. As with the style, there are clear differences between the functions of NTT and the HAF/BEE1/BEE3 genes within the ovary. For example, all ECM production appears absent from ntt mutants, but some residual staining is still present in haf bee1 bee3 mutants. Moreover, some pollen tubes penetrate the transmitting tract within the ovary in haf bee1 bee3 mutants, whereas this never occurs in ntt mutants. It is possible the decreased fertility in the ntt haf bee1 bee3 quadruple mutant compared with either the ntt mutant or haf bee1 bee3 triple mutant is caused by the severe ovary transmitting tract defect of the ntt mutant combined with the stylar-transmitting tract defect of the haf bee1 bee3 triple mutant.

We used a minimal-pollination assay to assess the efficiency of fertilization. Using this assay, we found that haf bee1 bee3 carpels were less efficient at producing seeds than wild type plants. Conversely, when HAF was misexpressed, fertilization efficiency was increased. To our knowledge, HAF is the first gene shown to be capable of increasing the potential of the carpel to be fertilized. It is worth noting that we were somewhat surprised to find, both here and in the earlier work involving ntt (Crawford, B. C. et al., *Curr Biol* 17:1101-8 (2007)), that wild-type carpels are relatively inefficient at producing seed when minimally pollinated. One explanation for these results is that there is normally an abundance of pollen, thus minimizing the requirement for all pollen tubes to complete their growth toward ovules (Williams, J. H., *American Journal of Botany* 96:144 (2009)). Indeed, it is possible the necessity to grow through the reproductive tract allows the maternal parent to select for the most robust pollen tubes that reach the ovules (Mulcahy, D., *Science* 206:20 (1979)).

Exactly how ectopic expression of HAF can lead to increased fertilization efficiency is unclear, although regulation of ECM production is certainly an important aspect. Recent studies have shown that the interaction between pollen tubes and reproductive tract dramatically changes the pollen transcriptome as well as the efficiency by which pollen tubes target ovules (Qin, Y. et al., *PLoS Genetics* 5, Article No.: e1000621 (2009)). Given the expression of HAF, BEE1 and BEE3 throughout the reproductive tract and the reduced fertilization efficiency of the triple mutant, it is possible that these genes function in the interaction of the reproductive tract with pollen tubes.

We found that the BFN1::GUS cell death marker (Farage-Barhom, S. et al., *J Exp Bot* 59:3247-58 (2008)) is expressed in the transmitting tract of wild-type carpels and that its expression is absent in the haf bee1 bee3 triple mutant. Previous studies involving a cytological analysis of the transmitting tract indicated that cell death begins around the time of fertilization and does not depend on the presence of pollen (Crawford, B. C. et al., *Curr Biol* 17:1101-8 (2007)). Confirming this result, we found that the BFN1::GUS marker is initially expressed just prior to fertilization (stage 13) and does not depend on pollination.

In addition to their importance in controlling cell death in the transmitting tract, HAF, BEE1 and BEE3 also influence cell death in the stigma (Carbonell-Bejerano, P. et al., *Plant Physiol* 154:163-72 (2010)). Stigmatic cells degenerate soon after pollination in wild type, but remain intact in haf bee1 bee3 mutants even 7 days post-anthesis. However, we did not find that the lack of stigmatic cell death in haf bee1 bee3 resulted in an increase in the post-emasculation period that stigmas were receptive to pollen.

Genes Regulating HAF Expression

We have identified a number of genes that function as upstream regulators of HAF expression. The NTT gene is required for ovary transmitting tract formation, and HAF expression is dramatically reduced in nu mutants. Moreover, AtML1>>HAF can partially rescue pollen tube growth in the ntt mutant. Although these data show that NTT acts upstream to promote HAF expression, HAF is still expressed at low levels in ntt mutants and the phenotype of nu mutants is further enhanced by mutations in haf, bee1 and bee3, suggesting that other factors also contribute to HAF expression.

We also show that wild-type HAF expression is dependent on the auxin pathway within the reproductive tract (Sundberg, E. and Ostergaard, L., *Cold Spring Harb Perspect Biol* 1: a001628 (2009)). The HEC genes, which encode bHLH proteins capable of interacting as heterodimers, are critical for formation of the reproductive tract (Gremski, K. et al., *Development* 134:3593-601 (2007)). HAF expression is dramatically decreased in hec mutants, indicating that HECs act upstream to promote HAF expression. HAF misexpression is also sufficient to partially restore the stigma and allow pollination in hec triple mutant carpels. The most closest-related gene to the HEC genes in *Arabidopsis* is INDEHISCENT (IND), and both the HECs and IND have been implicated in regulating auxin signaling (Gremski, K. et al., *Development* 134:3593-601 (2007); Liljegren, S. J. et al., *Cell* 116:843-53 (2004); Sorefan, K. et al., *Nature* (London) 459:583 (2009)). HAF expression is therefore dependent on the auxin signaling pathway.

The transcriptional response to auxin signaling is mediated by the ARF transcription factor family. The partially redundant ARF6 and ARF8 genes, which provide a link between auxin signaling and fruit development, are good candidates for ARF regulators of HAF expression (Nagpal, P. et al., *Development* 132:4107-18 (2005)). The fruit of arf6 arf8 mutants fail to stain for ECM, develop seeds primarily at their apical ends, and show a dramatic reduction in HAF expression. Moreover, the fertility defects of arf6 arf8 double mutants are similar to those seen in arf6 arf8 haf bee1 bee3 quintuple mutants, suggesting that all of these genes act in the same pathway. Taken together, the data suggest that ARF6 and ARF8 are essential for promoting HAF expression and for reproductive tract development.

We have shown that the normal expression pattern of HAF is dependent on several genes and that misexpression of HAF can partially rescue ntt and hec1 hec2 hec3 mutants. Although these data strongly suggest that HAF acts downstream of these genes, we cannot exclude the possibility that HAF acts at least partially in a parallel pathway. For example, the reduction in HAF expression in these mutants could be caused in part by the corresponding reduction or loss of reproductive tract tissues. The STYLISH genes, which have been implicated in controlling the expression of auxin biosynthesis genes, provide additional evidence for the important role for auxin in the development of the reproductive tract since these tissues are dramatically reduced in stylish mutants (Eklund, D. M. et al., *Plant Cell* 22:349-363 (2009)). Taken together, these data suggests that auxin controls HAF expression through the combined action of the STY, HEC and ARF6/8 genes.

In addition to auxin-mediated transcriptional control through ARF transcription factors, BEE1 and BEE3 have also been implicated in posttranslational control by atypical bHLH proteins regulating brassinosteroid signaling (Wang, H. et al., *Plant Cell* 21:3781-3791 (2009)). Recent work further suggests that HAF is regulated post translationally by BIN2, a kinase associated with brassinosteroid signaling (Poppenberger, B. et al., *Embo J* 30:1149-61 (2011)). Thus, while auxin likely controls transcription of HAF, BEE1 and BEE3 through ARF6 and ARF8, post-translational control could involve brassinosteroids. Given their roles in controlling the expression of these bHLH genes, it will be interesting to examine further the role of auxin and brassinosteroids in producing a fully functioning reproductive tract.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

Primers used

| Primer name | | Primer sequence (5'-3') | Primer name | Primer sequence (5'-3') |
|---|---|---|---|---|
| WT | HAF-X7 | GGCACGGTTTGAGCCATA (SEQ ID NO: 13) | HAF - X8 | CATCAAGCATCACTGCCATT (SEQ ID NO: 14) |
| MUTANT | DS3-2 | CGATTACCGTATTTATCCCGTTC (SEQ ID NO: 15) | HAF - X8 | CATCAAGCATCACTGCCATT (SEQ ID NO: 14) |

TABLE 1-continued

Primers used

| | Primer name | Primer sequence (5'-3') | Primer name | Primer sequence (5'-3') |
|---|---|---|---|---|
| WT | BEE1+ | GGTTCTTTGAGAAGAG GTAAGAGGT (SEQ ID NO: 16) | BEE1- | CTGCATGGAATCAACTGC ATCT (SEQ ID NO: 17) |
| MUTANT | JMLB2 | TTGGGTGATGGTTCAC GTAGTGGG (SEQ ID NO: 18) | BEE1+ | GGTTCTTTGAGAAGAGGT AAGAGGT (SEQ ID NO: 16) |
| WT | BEE5+ | CTCCTTTCTCTTCTTCT CTCGATTC (SEQ ID NO: 19) | BEE6- | TCAAGCATAGTAGCCATT CCCA (SEQ ID NO: 20) |
| MUTANT | JMLB2 | TTGGGTGATGGTTCAC GTAGTGGG (SEQ ID NO: 18) | BEE5+ | CTCCTTTCTCTTCTTCTCT CGATTC (SEQ ID NO: 19) |
| | 25330PROM1+ | AAGCTTATTAATATGT TCTCTTTCTAATTGTAA TTAAAA (SEQ ID NO: 21) | 25330PROMO3- | GGATCC TAGAGACACTACAAATTA AATCAAAATATGA (SEQ ID NO: 22) |
| | HAFCDNA+ | ATGGCACGGTTTGAGC CATATA (SEQ ID NO: 23) | HAFCDNA- | TCAAA AGGGTAATGTTGAACTGA A (SEQ ID NO: 24) |
| | HAFPOP1+ | GGTACCATGGCACGGT TTGAGCCATATA (SEQ ID NO: 25) | HAFPOP1- | AAGCTTTC AAAAGGGTAATGTTGAA CTGAA (SEQ ID NO: 26) |
| | BEE1PROMO1+ | AAGCTTACCTAGAGAG GGACCGTAAC (SEQ ID NO: 27) | BEE1PROMO2- | GGATCCAATATAATGAAT TGAGATATG (SEQ ID NO: 28) |
| | BEE3PROMO11+ | CTGCAG CCAATCAACATCACAA CAGAGACG (SEQ ID NO: 29) | BEE3PROMO2- | GGATCC TTCTGAGTTTCAATTTTTA TTTTTTTTTGAAAATTGG (SEQ ID NO: 30) |
| WT | HEC2LP | CCTCTGTCTTCCACCA TCATC (SEQ ID NO: 31) | HEC2RP | TGCATCAAGAACGTACCA CAG (SEQ ID NO: 32) |
| MUTANT | HEC2RP | TGCATCAAGAACGTAC CACAG (SEQ ID NO: 32) | DSPM1 | CTTATTTCAGTAAGAGTG TGGGGTTTTGG (SEQ ID NO: 33) |

What is claimed is:

1. A plant comprising a heterologous expression cassette, the expression cassette comprising a reproductive tissue-specific or an epidermal-specific promoter operably linked to a polynucleotide, wherein the polynucleotide encodes a polypeptide that is at least 90% identical to SEQ ID NO:2, wherein the plant has increased expression of the polypeptide compared to expression of the polypeptide in a non-transgenic control plant and wherein the plant exhibits one or more of increased fertilization efficiency, increased fruit size and/or parthenocarpy as compared to a non-transgenic control plant and wherein the increased fertilization efficiency is increased number of fertilized seeds per carpel.

2. The plant of claim 1, wherein the polynucleotide encodes a polypeptide that is at least 95% identical to SEQ ID NO:2.

3. The plant of claim 2, wherein the polynucleotide encodes a polypeptide that comprises SEQ ID NO:2.

4. The plant of claim 1, wherein the promoter is tissue an epidermal-specific promoter.

5. The plant of claim 1, wherein the promoter is a reproductive tissue-specific promoter.

6. The plant of claim 1, wherein the plant is a fruit-bearing crop plant.

7. A plant cell from the plant of claim 1.

8. A seed, flower, leaf, or fruit from the plant of claim 1, wherein the seed, flower, leaf or fruit comprise said expression cassette.

9. An expression cassette comprising a heterologous reproductive tissue-specific, or epidermal-specific promoter operably linked to a polynucleotide, wherein the polynucleotide encodes a polypeptide that is at least 90% identical to SEQ ID NO:2, wherein introduction of the expression cassette into a plant results in the plant having one Or more of increased fertilization efficiency, increased fruit size and/or parthenocarpy, and wherein the increased fertilization efficiency is increased number of fertilized seeds per carpel, as compared to a non-transgenic control plant.

10. The expression cassette of claim 9, wherein the polynucleotide encodes a polypeptide that is at least 95% identical to SEQ ID NO:2.

11. The expression cassette of claim 9, wherein the promoter is an epidermal-specific promoter.

12. The expression cassette of claim 9, wherein the promoter is a reproductive tissue-specific promoter.

13. An expression vector comprising the expression cassette of claim 9.

14. The expression cassette of claim 9, wherein the polynucleotide encodes a polypeptide that comprises SEQ ID NO:2.

* * * * *

SEQUENCE LISTING

<160> NUMBER OF SEQ ID NOS: 33

<210> SEQ ID NO 1
<211> LENGTH: 672
<212> TYPE: DNA
<213> ORGANISM: Arabidopsis thaliana
<220> FEATURE:
<223> OTHER INFORMATION: thale cress basic helix-loop-helix (bHLH)
      transcription factor HALF FILLED (HAF) At1g25330 cDNA

<400> SEQUENCE: 1

```
atggcacggt tgagccata taactataat aatggtcatg atcctttctt tgcacacatt      60
aaccaaaatc cagagctaat aaatctggac ttaccagctt ctaccccttc cagtttcatg     120
cttttctcca atggagcttt agttgatgcc aatcacaata attctcactt cttcccaaat     180
ttattgcacg gtaatacgag aagaaaagga aataaagaag agagtgggtc gaagagaaga     240
agaaagaggt cggaagagga agaagccatg aatggagatg agactcagaa gccaaaagat     300
gttgttcatg tccgagctaa gagaggtcaa gctactgata gccatagttt ggctgaaagg     360
```

```
gtacgaagag agaagatcaa tgaaaggctg aaatgcttac aagaccttgt tccaggatgc     420
tacaaggcaa tgggaatggc agtgatgctt gatgtcatca tagattatgt acgatcactc    480
cagaatcaaa tcgagttttt gtccatgaaa ctctcagcgg caagtgcatg ttacgacctt    540
aattctttgg atattgagcc aacggatata tttcagggag ggaatattca tagtgcagca    600
gagatggaaa ggattttaag agaaagcgtt ggaacacagc ctcctaattt cagttcaaca    660 ttacccttt ga                                                         672
```

```
<210> SEQ ID NO 2
<211> LENGTH: 223
<212> TYPE: PRT
<213> ORGANISM: Arabidopsis thaliana
<220> FEATURE:
<223> OTHER INFORMATION: thale cress basic helix-loop-helix (bHLH)
      transcription factor HALF FILLED (HAF) At1g25330
<220> FEATURE:
<221> NAME/KEY: DOMAIN
<222> LOCATION: (115)...(161)
<223> OTHER INFORMATION: bHLH protein subdomain

<400> SEQUENCE: 2

Met Ala Arg Phe Glu Pro Tyr Asn Tyr Asn Asn Gly His Asp Pro Phe
 1               5                  10                  15

Phe Ala His Ile Asn Gln Asn Pro Glu Leu Ile Asn Leu Asp Leu Pro
            20                  25                  30

Ala Ser Thr Pro Ser Ser Phe Met Leu Phe Ser Asn Gly Ala Leu Val
        35                  40                  45

Asp Ala Asn His Asn Asn Ser His Phe Phe Pro Asn Leu Leu His Gly
    50                  55                  60

Asn Thr Arg Arg Lys Gly Asn Lys Glu Glu Ser Gly Ser Lys Arg Arg
65                  70                  75                  80

Arg Lys Arg Ser Glu Glu Glu Ala Met Asn Gly Asp Glu Thr Gln
                85                  90                  95

Lys Pro Lys Asp Val Val His Val Arg Ala Lys Arg Gly Gln Ala Thr
            100                 105                 110

Asp Ser His Ser Leu Ala Glu Arg Val Arg Arg Glu Lys Ile Asn Glu
        115                 120                 125

Arg Leu Lys Cys Leu Gln Asp Leu Val Pro Gly Cys Tyr Lys Ala Met
    130                 135                 140

Gly Met Ala Val Met Leu Asp Val Ile Ile Asp Tyr Val Arg Ser Leu
145                 150                 155                 160

Gln Asn Gln Ile Glu Phe Leu Ser Met Lys Leu Ser Ala Ala Ser Ala
                165                 170                 175

Cys Tyr Asp Leu Asn Ser Leu Asp Ile Glu Pro Thr Asp Ile Phe Gln
            180                 185                 190

Gly Gly Asn Ile His Ser Ala Ala Glu Met Glu Arg Ile Leu Arg Glu
        195                 200                 205

Ser Val Gly Thr Gln Pro Pro Asn Phe Ser Ser Thr Leu Pro Phe
    210                 215                 220
```

```
<210> SEQ ID NO 3
<211> LENGTH: 783
<212> TYPE: DNA
<213> ORGANISM: Arabidopsis thaliana
<220> FEATURE:
<223> OTHER INFORMATION: thale cress basic helix-loop-helix (bHLH)
      transcription factor BRASSINOSTEROID ENHANCED EXPRESSION 1 (BEE1)
      At1g18400 cDNA
```

<400> SEQUENCE: 3

```
atggcaaatt tcgagaatct ttcttctgat tttcagacaa tagccatgga tatatattct    60
tccataactc aagctgcaga tctaaacaac aacaacagta accttcattt tcaaacattt   120
catccttcct ctactctct cgaatcgctc ttccttcatc atcatcaaca acaattactt   180
cactttcccg aaactctcc agacagtagt aacaatttct cttcaacttc aagtttcctc   240
catagtgatc acaacatcgt cgatgagacc aagaagagaa aagctttgtt acctactttg   300
tcttcatcag agactagcgg cgtctccgat aatacgaatg ttattgccac tgaaacaggt   360
tctttgagaa gaggtaagag gttgaagaag aagaaggaag aagaagacga aaagagaga   420
gaagttgttc atgtgagagc cagaagaggc caagccactg atagccacag cttagcagaa   480
cgggttcggc gagggaaaat aaacgagaga ttaagatgct tgcaagatat ggtgcccgga   540
tgttataagg ctatgggaat ggctacgatg cttgacgaga taattaatta tgtccagtct   600
ctacagaatc aagtcgagtt cctctcgatg aaactcactg cagcaagttc gttttatgac   660
tttaactcag agacagatgc agttgattcc atgcagagag caaaggcacg tgagacagtg   720
gagatgggga gacaaacaag agatgggagt cctgtcttcc atttatcaac atggtccctt   780
tga                                                                 783
```

<210> SEQ ID NO 4
<211> LENGTH: 260
<212> TYPE: PRT
<213> ORGANISM: Arabidopsis thaliana
<220> FEATURE:
<223> OTHER INFORMATION: thale cress basic helix-loop-helix (bHLH) transcription factor BRASSINOSTEROID ENHANCED EXPRESSION 1 (BEE1) At1g18400
<220> FEATURE:
<221> NAME/KEY: DOMAIN
<222> LOCATION: (155)...(202)
<223> OTHER INFORMATION: bHLH protein subdomain

<400> SEQUENCE: 4

```
Met Ala Asn Phe Glu Asn Leu Ser Ser Asp Phe Gln Thr Ile Ala Met
  1               5                  10                  15

Asp Ile Tyr Ser Ser Ile Thr Gln Ala Ala Asp Leu Asn Asn Asn Asn
             20                  25                  30

Ser Asn Leu His Phe Gln Thr Phe His Pro Ser Ser Thr Ser Leu Glu
         35                  40                  45

Ser Leu Phe Leu His His His Gln Gln Gln Leu Leu His Phe Pro Gly
     50                  55                  60

Asn Ser Pro Asp Ser Ser Asn Asn Phe Ser Ser Thr Ser Ser Phe Leu
 65                  70                  75                  80

His Ser Asp His Asn Ile Val Asp Glu Thr Lys Lys Arg Lys Ala Leu
                 85                  90                  95

Leu Pro Thr Leu Ser Ser Ser Glu Thr Ser Gly Val Ser Asp Asn Thr
            100                 105                 110

Asn Val Ile Ala Thr Glu Thr Gly Ser Leu Arg Arg Gly Lys Arg Leu
        115                 120                 125

Lys Lys Lys Lys Glu Glu Glu Asp Glu Lys Glu Arg Glu Val Val His
    130                 135                 140

Val Arg Ala Arg Arg Gly Gln Ala Thr Asp Ser His Ser Leu Ala Glu
145                 150                 155                 160

Arg Val Arg Arg Gly Lys Ile Asn Glu Arg Leu Arg Cys Leu Gln Asp
                165                 170                 175
```

```
Met Val Pro Gly Cys Tyr Lys Ala Met Gly Met Ala Thr Met Leu Asp
            180                 185                 190

Glu Ile Ile Asn Tyr Val Gln Ser Leu Gln Asn Gln Val Glu Phe Leu
        195                 200                 205

Ser Met Lys Leu Thr Ala Ala Ser Ser Phe Tyr Asp Phe Asn Ser Glu
    210                 215                 220

Thr Asp Ala Val Asp Ser Met Gln Arg Ala Lys Ala Arg Glu Thr Val
225                 230                 235                 240

Glu Met Gly Arg Gln Thr Arg Asp Gly Ser Pro Val Phe His Leu Ser
                245                 250                 255

Thr Trp Ser Leu
            260

<210> SEQ ID NO 5
<211> LENGTH: 786
<212> TYPE: DNA
<213> ORGANISM: Arabidopsis thaliana
<220> FEATURE:
<223> OTHER INFORMATION: thale cress basic helix-loop-helix (bHLH)
      transcription factor BRASSINOSTEROID ENHANCED EXPRESSION 3 (BEE3)
      At1g73830 cDNA

<400> SEQUENCE: 5
atggcgaatc tctcttctga ttttcagaca tttacaatgg atgatcccat aagacaacta      60
gcagaactga gcaacacgct tcatcatttc caaacatttc ctcctccttt ctcttcttct    120
ctcgattctc ttttctttca taatcaattc cctgatcatt ttcccggaaa atctctcgag    180 aataatttc atcaagggat attcttccct tctaatatcc aaaacaacga agagtcttct     240
tcacaattcg ataccaagaa gagaaaatca ttaatggaag ctgtttctac gtcggagaac    300
agtgtctctg atcaaactct ctctacctct tctgctcaag tttccataaa tggaaatatt    360
tcgacaaaaa ataattcttc aaggagaggg aagaggtcga agaatagaga agaagagaaa    420
gagagagaag ttgttcatgt tagagctaga agaggccaag ccactgatag ccacagcata    480
gcagaacggg ttcgacgagg gaaaataaac gagagattga atgcttgca agatatagtc     540 cccggatgtt ataagacaat gggaatggct actatgcttg atgagataat taattacgtc    600
cagtccttac aaaatcaagt cgagtttta tctatgaagc ttacagcagc aagttcgtat    660
tatgacttta actcggagac tgatgctgtg aatccatgc agaaggcaaa ggcacgtgag    720
gcagtggaga tgggtcaagg gagggatggg agttctgtct tccattcatc atcgtggacc    780
ctttga                                                              786

<210> SEQ ID NO 6
<211> LENGTH: 261
<212> TYPE: PRT
<213> ORGANISM: Arabidopsis thaliana
<220> FEATURE:
<223> OTHER INFORMATION: thale cress basic helix-loop-helix (bHLH)
      transcription factor BRASSINOSTEROID ENHANCED EXPRESSION 3 (BEE3)
      At1g73830
<220> FEATURE:
<221> NAME/KEY: DOMAIN
<222> LOCATION: (157)...(204)
<223> OTHER INFORMATION: bHLH protein suubdomain

<400> SEQUENCE: 6

Met Ala Asn Leu Ser Ser Asp Phe Gln Thr Phe Thr Met Asp Asp Pro
1               5                   10                  15

Ile Arg Gln Leu Ala Glu Leu Ser Asn Thr Leu His His Phe Gln Thr
```

```
                    20                  25                  30
Phe Pro Pro Pro Phe Ser Ser Ser Leu Asp Ser Leu Phe Phe His Asn
            35                  40                  45

Gln Phe Pro Asp His Phe Pro Gly Lys Ser Leu Glu Asn Asn Phe His
        50                  55                  60

Gln Gly Ile Phe Phe Pro Ser Asn Ile Gln Asn Asn Glu Glu Ser Ser
 65                  70                  75                  80

Ser Gln Phe Asp Thr Lys Lys Arg Lys Ser Leu Met Glu Ala Val Ser
                    85                  90                  95

Thr Ser Glu Asn Ser Val Ser Asp Gln Thr Leu Ser Thr Ser Ser Ala
            100                 105                 110

Gln Val Ser Ile Asn Gly Asn Ile Ser Thr Lys Asn Asn Ser Ser Arg
        115                 120                 125

Arg Gly Lys Arg Ser Lys Asn Arg Glu Glu Lys Glu Arg Glu Val
        130                 135                 140

Val His Val Arg Ala Arg Arg Gly Gln Ala Thr Asp Ser His Ser Ile
145                 150                 155                 160

Ala Glu Arg Val Arg Arg Gly Lys Ile Asn Glu Arg Leu Lys Cys Leu
                165                 170                 175

Gln Asp Ile Val Pro Gly Cys Tyr Lys Thr Met Gly Met Ala Thr Met
            180                 185                 190

Leu Asp Glu Ile Ile Asn Tyr Val Gln Ser Leu Gln Asn Gln Val Glu
        195                 200                 205

Phe Leu Ser Met Lys Leu Thr Ala Ala Ser Ser Tyr Tyr Asp Phe Asn
        210                 215                 220

Ser Glu Thr Asp Ala Val Glu Ser Met Gln Lys Ala Lys Ala Arg Glu
225                 230                 235                 240

Ala Val Glu Met Gly Gln Gly Arg Asp Gly Ser Ser Val Phe His Ser
                245                 250                 255

Ser Ser Trp Thr Leu
            260

<210> SEQ ID NO 7
<211> LENGTH: 777
<212> TYPE: DNA
<213> ORGANISM: Vitis vinifera
<220> FEATURE:
<223> OTHER INFORMATION: grape basic helix-loop-helix (bHLH)
      transcription factor HALF FILLED (HAF)-like cDNA

<400> SEQUENCE: 7
atggcagagt ttgcagcaaa cttgcagagc cttaaacctt cttccttaga aatgaactca      60
aacatggaac tgatgaacaa ccggagtgca ccagagaatt cccacatgaa tggtcacgga     120
ttcatggctt tctccaatgt gggattctct atacatcacc aacaagagtt ccctgtgaac     180
ttcagggata atactcaaag ccctgttcat gctggaggtc taagtgctgt ccaagttctt     240
cagttctcat cgcagcccgg agattttggc caggaaacaa agactggaaa agtgaatttt     300
gtatcatctc ctccagcttc tgggtctgag ttccttggag ataataagaa cttgggtgga     360
agaaagagga gagaagcaa tgagagaaa acaataaac caagagaagt tatccatgtg      420
agagcaaaga gaggccaagc tactgatagt cacagtttgg cagaaagggt aagaagagag     480
aaaataaacg agaaactgag atgcttgcag gacctggttc caggatgcta taagactatg     540
ggaatggctg tgatgttgga tgtgataatc aattatgtcc agtcactgca gaaccagatt     600
gaatttctct ctatgaagct ttcagcagca agcaccttct atgacttcaa ctcatcagag     660
```

```
gcagaagctt tggaaaccat gcaggggaca aatgcatatg aggtacatga ggtggagagg    720
tcggtgaaag aagggtatgg agggccttct catctccact caacatggcc tttttga      777
```

<210> SEQ ID NO 8
<211> LENGTH: 258
<212> TYPE: PRT
<213> ORGANISM: Vitis vinifera
<220> FEATURE:
<223> OTHER INFORMATION: grape basic helix-loop-helix (bHLH)
      transcription factor HALF FILLED (HAF)-like

<400> SEQUENCE: 8

Met Ala Glu Phe Ala Ala Asn Leu Gln Ser Leu Lys Pro Ser Ser Leu
 1               5                  10                  15

Glu Met Asn Ser Asn Met Glu Leu Met Asn Asn Arg Ser Ala Pro Glu
            20                  25                  30

Asn Ser His Met Asn Gly His Gly Phe Met Ala Phe Ser Asn Val Gly
        35                  40                  45

Phe Ser Ile His His Gln Gln Glu Phe Pro Val Asn Phe Arg Asp Asn
    50                  55                  60

Thr Gln Ser Pro Val His Ala Gly Gly Leu Ser Ala Val Gln Val Leu
65                  70                  75                  80

Gln Phe Ser Ser Gln Pro Gly Asp Phe Gly Gln Glu Thr Lys Thr Gly
                85                  90                  95

Lys Val Asn Phe Val Ser Ser Pro Ala Ser Gly Ser Glu Phe Leu
            100                 105                 110

Gly Asp Asn Lys Asn Leu Gly Gly Arg Lys Arg Lys Arg Ser Asn Glu
        115                 120                 125

Arg Glu Asn Asn Lys Pro Arg Glu Val Ile His Val Arg Ala Lys Arg
    130                 135                 140

Gly Gln Ala Thr Asp Ser His Ser Leu Ala Glu Arg Val Arg Arg Glu
145                 150                 155                 160

Lys Ile Asn Glu Lys Leu Arg Cys Leu Gln Asp Leu Val Pro Gly Cys
                165                 170                 175

Tyr Lys Thr Met Gly Met Ala Val Met Leu Asp Val Ile Ile Asn Tyr
            180                 185                 190

Val Gln Ser Leu Gln Asn Gln Ile Glu Phe Leu Ser Met Lys Leu Ser
        195                 200                 205

Ala Ala Ser Thr Phe Tyr Asp Phe Asn Ser Ser Glu Ala Glu Ala Leu
    210                 215                 220

Glu Thr Met Gln Gly Thr Asn Ala Tyr Glu Val His Glu Val Glu Arg
225                 230                 235                 240

Ser Val Lys Glu Gly Tyr Gly Gly Pro Ser His Leu His Ser Thr Trp
                245                 250                 255

Pro Phe

<210> SEQ ID NO 9
<211> LENGTH: 657
<212> TYPE: DNA
<213> ORGANISM: Solanum lycopersicum
<220> FEATURE:
<223> OTHER INFORMATION: tomato basic helix-loop-helix (bHLH)
      transcription factor HALF FILLED (HAF)-like cDNA

<400> SEQUENCE: 9

```
atgtctaatt tcataatga tcatcatatg aataatatta gccatgatgt ttatgatccc    60
```

```
gccgtcgcgg ttgctgctgc tcaattttt actttgggag gtccaagtta tggatgtact    120
agctcaattc cagaatcaga atccatgttg aatagtagta ataataacat taatattcca   180
actcctcatc ctctagtctc tggaaatact actagcaaga atacaagtga agggagaaag   240
agaaaaagga acaatcaaaa ggaagttgag aaaccaagag aagttgtcca tgttagagca   300
aagagaggcc aagctactga tagtcatagt ttggctgaaa gacttcgaag ggagaaaata   360
aatgaaaaac tcagatgctt gcaagaactt gttcctggat gttataagac tatgggaatg   420
gcagtgatgt tagatgtaat aatcaattac gtccggtcat tgcaaaatca aattgatttt   480
ctttcaatga aactatcagc agcaagtttg ttttatgatt tcaattcatc agagatggat   540
gatatggact caatgcaggg aacaaatggg tatgcagcag ctcaaggaat ggggaaaaat   600
attgttggag aagggtatgg aggatttcct caatttcaaa catcttggcc tctttaa     657
```

<210> SEQ ID NO 10
<211> LENGTH: 218
<212> TYPE: PRT
<213> ORGANISM: Solanum lycopersicum
<220> FEATURE:
<223> OTHER INFORMATION: tomato basic helix-loop-helix (bHLH)
      transcription factor HALF FILLED (HAF)-like <400> SEQUENCE: 10

```
Met Ser Asn Phe His Asn Asp His His Met Asn Asn Ile Ser His Asp
 1               5                  10                  15

Val Tyr Asp Pro Ala Val Ala Val Ala Ala Gln Phe Phe Thr Leu
            20                  25                  30

Gly Gly Pro Ser Tyr Gly Cys Thr Ser Ile Pro Glu Ser Glu Ser
        35                  40                  45

Met Leu Asn Ser Ser Asn Asn Asn Ile Asn Ile Pro Thr Pro His Pro
 50                  55                  60

Leu Val Ser Gly Asn Thr Thr Ser Lys Asn Thr Ser Glu Gly Arg Lys
 65                  70                  75                  80

Arg Lys Arg Asn Asn Gln Lys Glu Val Glu Lys Pro Arg Glu Val Val
                 85                  90                  95

His Val Arg Ala Lys Arg Gly Gln Ala Thr Asp Ser His Ser Leu Ala
            100                 105                 110

Glu Arg Leu Arg Arg Glu Lys Ile Asn Glu Lys Leu Arg Cys Leu Gln
        115                 120                 125

Glu Leu Val Pro Gly Cys Tyr Lys Thr Met Gly Met Ala Val Met Leu
130                 135                 140

Asp Val Ile Ile Asn Tyr Val Arg Ser Leu Gln Asn Gln Ile Asp Phe
145                 150                 155                 160

Leu Ser Met Lys Leu Ser Ala Ala Ser Leu Phe Tyr Asp Phe Asn Ser
                165                 170                 175

Ser Glu Met Asp Asp Met Asp Ser Met Gln Gly Thr Asn Gly Tyr Ala
            180                 185                 190

Ala Ala Gln Gly Met Gly Lys Asn Ile Val Gly Glu Gly Tyr Gly Gly
        195                 200                 205

Phe Pro Gln Phe Gln Thr Ser Trp Pro Leu
    210                 215
```

<210> SEQ ID NO 11
<211> LENGTH: 15
<212> TYPE: DNA
<213> ORGANISM: Artificial Sequence
<220> FEATURE:

```
<223> OTHER INFORMATION: synthetic polynucleotide encoding amino acid
      sequence SEQ ID NO:12

<400> SEQUENCE: 11
atgatggagc atcat                                                      15

<210> SEQ ID NO 12
<211> LENGTH: 5
<212> TYPE: PRT
<213> ORGANISM: Artificial Sequence
<220> FEATURE:
<223> OTHER INFORMATION: synthetic polypeptide encoded by polynucleotide
      sequence SEQ ID NO:11

<400> SEQUENCE: 12

Met Met Glu His His
 1               5

<210> SEQ ID NO 13
<211> LENGTH: 18
<212> TYPE: DNA
<213> ORGANISM: Artificial Sequence
<220> FEATURE:
<223> OTHER INFORMATION: synthetic WT primer HAF-X7

<400> SEQUENCE: 13
ggcacggttt gagccata                                                   18

<210> SEQ ID NO 14
<211> LENGTH: 20
<212> TYPE: DNA
<213> ORGANISM: Artificial Sequence
<220> FEATURE:
<223> OTHER INFORMATION: synthetic WT primer HAF-X8

<400> SEQUENCE: 14
catcaagcat cactgccatt                                                 20

<210> SEQ ID NO 15
<211> LENGTH: 23
<212> TYPE: DNA
<213> ORGANISM: Artificial Sequence
<220> FEATURE:
<223> OTHER INFORMATION: synthetic MUTANT primer DS3-2

<400> SEQUENCE: 15
cgattaccgt atttatcccg ttc                                             23

<210> SEQ ID NO 16
<211> LENGTH: 25
<212> TYPE: DNA
<213> ORGANISM: Artificial Sequence
<220> FEATURE:
<223> OTHER INFORMATION: synthetic WT and MUTANT primer BEE1+

<400> SEQUENCE: 16
ggttctttga gaagaggtaa gaggt                                           25

<210> SEQ ID NO 17
<211> LENGTH: 22
<212> TYPE: DNA
<213> ORGANISM: Artificial Sequence
<220> FEATURE:
<223> OTHER INFORMATION: synthetic WT primer BEE1-

<400> SEQUENCE: 17
```
ctgcatggaa tcaactgcat ct                                                   22

<210> SEQ ID NO 18
<211> LENGTH: 24
<212> TYPE: DNA
<213> ORGANISM: Artificial Sequence
<220> FEATURE:
<223> OTHER INFORMATION: synthetic MUTANT primer JMLB2

<400> SEQUENCE: 18
ttgggtgatg gttcacgtag tggg                                                 24

<210> SEQ ID NO 19
<211> LENGTH: 25
<212> TYPE: DNA
<213> ORGANISM: Artificial Sequence
<220> FEATURE:
<223> OTHER INFORMATION: synthetic WT and MUTANT primer BEE5+

<400> SEQUENCE: 19
ctcctttctc ttcttctctc gattc                                                25

<210> SEQ ID NO 20
<211> LENGTH: 22
<212> TYPE: DNA
<213> ORGANISM: Artificial Sequence
<220> FEATURE:
<223> OTHER INFORMATION: synthetic WT primer BEE6-

<400> SEQUENCE: 20
tcaagcatag tagccattcc ca                                                   22

<210> SEQ ID NO 21
<211> LENGTH: 39
<212> TYPE: DNA
<213> ORGANISM: Artificial Sequence
<220> FEATURE:
<223> OTHER INFORMATION: synthetic primer 25330PROM1+

<400> SEQUENCE: 21
aagcttatta atatgttctc tttctaattg taattaaaa                                 39

<210> SEQ ID NO 22
<211> LENGTH: 37
<212> TYPE: DNA
<213> ORGANISM: Artificial Sequence
<220> FEATURE:
<223> OTHER INFORMATION: synthetic primer 25330PROM1-

<400> SEQUENCE: 22
ggatcctaga gacactacaa attaaatcaa aatatga                                   37

<210> SEQ ID NO 23
<211> LENGTH: 22
<212> TYPE: DNA
<213> ORGANISM: Artificial Sequence
<220> FEATURE:
<223> OTHER INFORMATION: synthetic primer HAFCDNA+

<400> SEQUENCE: 23
atggcacggt ttgagccata ta                                                   22

<210> SEQ ID NO 24
<211> LENGTH: 24
<212> TYPE: DNA
<213> ORGANISM: Artificial Sequence
<220> FEATURE:
<223> OTHER INFORMATION: synthetic primer HAFCDNA-

<400> SEQUENCE: 24
tcaaaagggt aatgttgaac tgaa                                            24

<210> SEQ ID NO 25
<211> LENGTH: 28
<212> TYPE: DNA
<213> ORGANISM: Artificial Sequence
<220> FEATURE:
<223> OTHER INFORMATION: synthetic primer HAFPOP1+

<400> SEQUENCE: 25
ggtaccatgg cacggtttga gccatata                                        28

<210> SEQ ID NO 26
<211> LENGTH: 30
<212> TYPE: DNA
<213> ORGANISM: Artificial Sequence
<220> FEATURE:
<223> OTHER INFORMATION: synthetic primer HAFPOP1-

<400> SEQUENCE: 26
aagctttcaa aagggtaatg ttgaactgaa                                      30

<210> SEQ ID NO 27
<211> LENGTH: 26
<212> TYPE: DNA
<213> ORGANISM: Artificial Sequence
<220> FEATURE:
<223> OTHER INFORMATION: synthetic primer BEE1PROMO1+

<400> SEQUENCE: 27
aagcttacct agagagggac cgtaac                                          26

<210> SEQ ID NO 28
<211> LENGTH: 27
<212> TYPE: DNA
<213> ORGANISM: Artificial Sequence
<220> FEATURE:
<223> OTHER INFORMATION: synthetic primer BEE1PROMO2-

<400> SEQUENCE: 28
ggatccaata taatgaattg agatatg                                         27

<210> SEQ ID NO 29
<211> LENGTH: 30
<212> TYPE: DNA
<213> ORGANISM: Artificial Sequence
<220> FEATURE:
<223> OTHER INFORMATION: synthetic primer BEE3PROMO11+

<400> SEQUENCE: 29
ctgcagccaa tcaacatcac aacagagacg                                      30

<210> SEQ ID NO 30
<211> LENGTH: 44
<212> TYPE: DNA
<213> ORGANISM: Artificial Sequence
<220> FEATURE:
<223> OTHER INFORMATION: synthetic primer BEE3PROMO2-

<400> SEQUENCE: 30
ggatccttct gagtttcaat ttttattttt tttttgaaaa ttgg                      44

```
<210> SEQ ID NO 31
<211> LENGTH: 21
<212> TYPE: DNA
<213> ORGANISM: Artificial Sequence
<220> FEATURE:
<223> OTHER INFORMATION: synthetic WT primer HEC2LP

<400> SEQUENCE: 31
cctctgtctt ccaccatcat c                                              21

<210> SEQ ID NO 32
<211> LENGTH: 21
<212> TYPE: DNA
<213> ORGANISM: Artificial Sequence
<220> FEATURE:
<223> OTHER INFORMATION: synthetic WT and MUTANT primer HEC2RP

<400> SEQUENCE: 32
tgcatcaaga acgtaccaca g                                              21

<210> SEQ ID NO 33
<211> LENGTH: 29
<212> TYPE: DNA
<213> ORGANISM: Artificial Sequence
<220> FEATURE:
<223> OTHER INFORMATION: synthetic MUTANT primer DSPM1

<400> SEQUENCE: 33
cttatttcag taagagtgtg gggttttgg                                      29
```